US008067556B2

(12) United States Patent
Hogrefe et al.

(10) Patent No.: US 8,067,556 B2
(45) Date of Patent: Nov. 29, 2011

(54) MULTI-SITE MUTAGENESIS

(75) Inventors: Holly H. Hogrefe, San Diego, CA (US); Janice M. Cline, San Marcos, CA (US)

(73) Assignee: Agilent Technologies, Inc., Loveland, CO (US)

( * ) Notice: Subject to any disclaimer, the term of this patent is extended or adjusted under 35 U.S.C. 154(b) by 392 days.

(21) Appl. No.: 10/198,449

(22) Filed: Jul. 18, 2002

(65) Prior Publication Data

US 2006/0051748 A1     Mar. 9, 2006

Related U.S. Application Data

(60) Provisional application No. 60/307,927, filed on Jul. 26, 2001.

(51) Int. Cl.
    C07H 21/02     (2006.01)
    C07H 21/04     (2006.01)
    C12Q 1/68     (2006.01)
    C12P 19/34     (2006.01)

(52) U.S. Cl. .................. 536/23.1; 536/24.33; 536/24.3; 435/6; 435/91.1; 435/91.2; 435/91.51; 435/91.52

(58) Field of Classification Search ............... 435/91.51, 435/91.52, 6, 91.1, 91.2, 183; 436/94; 536/23.1, 536/24.3, 24.33, 25.3

See application file for complete search history.

(56) References Cited

U.S. PATENT DOCUMENTS

| | | | | |
|---|---|---|---|---|
| 5,478,724 A | * | 12/1995 | Morse et al. .................. | 435/5 |
| 5,494,810 A | | 2/1996 | Barany et al. | |
| 5,556,750 A | * | 9/1996 | Modrich et al. .................. | 435/6 |
| 5,648,482 A | * | 7/1997 | Meyer .................. | 536/24.33 |
| 5,942,391 A | * | 8/1999 | Zhang et al. .................. | 435/6 |
| 5,965,408 A | | 10/1999 | Short .................. | 435/91.1 |
| 6,063,566 A | * | 5/2000 | Joyce .................. | 435/6 |
| 6,117,679 A | | 9/2000 | Stemmer .................. | 435/440 |
| 6,132,970 A | | 10/2000 | Stemmer .................. | 435/6 |
| 6,165,793 A | | 12/2000 | Stemmer .................. | 435/440 |
| 6,180,406 B1 | | 1/2001 | Stemmer .................. | 435/440 |
| 6,221,603 B1 | * | 4/2001 | Mahtani .................. | 435/6 |
| 6,284,461 B1 | * | 9/2001 | Zlokarnik et al. .................. | 435/6 |
| 6,350,580 B1 | * | 2/2002 | Sorge .................. | 435/6 |
| 6,355,431 B1 | * | 3/2002 | Chee et al. .................. | 435/6 |
| 6,528,254 B1 | * | 3/2003 | Sorge .................. | 435/6 |
| 6,620,597 B1 | * | 9/2003 | Chen et al. .................. | 435/91.1 |

FOREIGN PATENT DOCUMENTS

| | | |
|---|---|---|
| EP | 1 178 109 A1 | 2/2002 |
| WO | WO 01/09347 A2 | 2/2001 |
| WO | WO 01/29211 A2 | 4/2001 |
| WO | WO 01/29212 A1 | 4/2001 |

OTHER PUBLICATIONS

1988 Stratagene catalog. Published by Straragene, 11011 North Torrey Pines Road, La Jolla, CA 92037.*
Frackman et al., Betain and DMSO: enhancing Agents for PCR. Promega Notes, 65, p. 27, 1998.*
Fricke et al., Slx1-Slx4 is a second structure-specific endonuclease functionally redundant with Sgs1-Top3. Genes & Dev., 17, 1768-1778, 2003.*
Attached definition of FEN-1 from Wikipedia, the free encyclopedia. Printed on Jan. 8, 2009.*
Hosfield et al., Newly Discovered Archaebacterial Flap Endonucleases Show a Structure-Specific Mechanism for DNA Substrate Binding and Catalysis Resembling Human Flap Endonuclease-1. The Journal of Biological Chemistry, 273, 27154-27161, 1998.*
Qiu et al., *Saccharomyces cerevisiae* RNase H(35) Functions in RNA Primer Removal during Lagging-Strand DNA Synthesis, Most Efficiently in Cooperation with Rad27 Nuclease. Molecular and Cellular Biology, 19, 8361-8371, 1999.*
1999 Stratagene Catalog, p. 170. Published by Stratagene Cloning Systems, 11011 North Torrey Pines Road, La Jolla, CA 92037, USA.*
Stemmer, W.P.C., (1994), "DNA shuffling by random fragmentation and reassembly: In vitro recombination for molecular evolution," *Proc. Natl. Acad. Sci. USA*, 91: 10747-10751.
Miyazaki, K., et al., (1999), "Exploring Nonnatural Evolutionary Pathways by Saturation Mutagenesis: Rapid Improvement of Protein Function," *Journal of Molecular Evolution*, 49: 716-720.
Kim, Y., et al., (2000), "Multiple Site Mutagenesis with High Targeting Efficiency in One Cloning Step," *BioTechniques*, 28(2): 196-198.
Sawano, A., et al., (2000), "Directed evolution of green fluorescent protein by a new versatile PCR strategy for site-directed and semi-random mutagenesis," *Nucleic Acids Research*, 28(16): e78(i-vii).
Coco, W.M., et al., (2001), "DNA shuffling method for generating highly recombined genes and evolved enzymes," *Nature Biotechnology*, 19: 354-359.
Moore, G.L., et al., (2001), "Predicting crossover generation in DNA shuffling," *Proc. Natl. Acad. Sci. USA*, 98(6): 3226-3231.
Whalen, et al., (2001), "DNA shuffling and vaccines," *Curr. Opin. Mol. Ther.*, 3: 31-36.
Matsumoto, Y. et al., (1999), "Reconstitution of Proliferating Cell Nuclear Antigen-dependent Repair of Apurinic/Apyrimidinic Sites with Purified Human Proteins", *The Journal of Biological Chemistry*, 274(47):33703-33708.
Pascucci, B. et al., (1999), "Long Patch Base Excision Repair with Purified Human Proteins", *The Journal of Biological Chemistry*, 274(47):33696-33702.
International Search Report of International Application No. PCT/US02/22759.

(Continued)

*Primary Examiner* — Frank W Lu

(57) ABSTRACT

The present invention provides compositions and improved methods for multi-site directed mutagenesis and DNA shuffling. The present compositions and methods provide increased mutation frequency and increased number of transformants which allow one to sequence only a few clones in order to identify the correct mutants and to obtain the desired mutant by screening large number of transformants in a short time. Moreover, the inclusion of FEN-1, PEF and optimized buffer and cycling conditions provided in the present invention should also facilitate random mutagenized library construction and the mutagenesis of large or difficult templates.

61 Claims, 15 Drawing Sheets

OTHER PUBLICATIONS

Stratagene 1988 Catalog, p. 39. Published by Stratagene Cloning Systems, 11011 North Torrey Pines Road, La Jolla, CA 92037.
International Preliminary Examination Report for PCT/US02/22759.
Kaiser, Michael W. et al., (1999), "A Comparison of Eubacterial and Archaeal Structure-specific 5'-Exonucleases", *The Journal of Biological Chemistry*, 274(30): 21387-21394.
Sawano, Asako et al., (2000), "Directed evolution of green fluorescent protein by a new versatile PCR strategy for site-directed and semi-random mutagenesis", *Oxford University Press*, 28(16): 1-7.
European Search Report of International Application No. PCT/US02/22759.

* cited by examiner

*lacZ* stop
(1.6-kb *Pfu* alkaline phosphatase gene)ATTAACGC *TTA*CAATTTC CATTCGCCAT TCAGGCTGCG

CAACTGTTGG GAAGGGCGAT CGGTGCGGGC CTCTTCGCTA TACGCCAGC TGGCGAAAGG

GGGATGTGCT GCAAGGCGAT TAAGTTGGGT AACGCCAGGG TTTTCCCAGT CACGACGTTG
                                                                                K
TAAAACGACG GCCAGTGAGC GCGCGTAATA CGACTCACTA TAGGGCGAAT TGGGTTACGG
                                      H
GCCCCCCCTC GA GGTCGACG GTATCGATTA GCTTGATATC GAATTCCTGC AGCCCGGGGG

ATCCACTAGT TCTAGAGCGG CCGCCACCGC GGTGGAGCTC CAGCTTTTGT TCCCTTTAGT
            QC                                *lacZ* start
GAGGGTTAAT TACGCGCTTG GCGTAATCAT GGT*CA*TAGCT GTTTCCTGTG TGAAATTGTT

ATCCGCTCAC AATTCCACAC AACATACGAG (SEQ ID NO: 21)

Figure 2

A. Final titration of *PfuTurbo* DNA polymerase
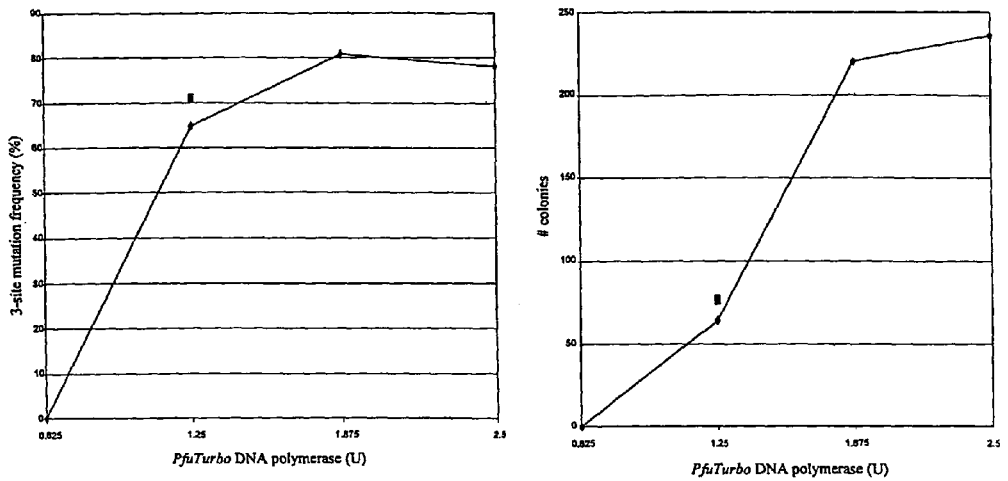
B. Final titration of FEN-1
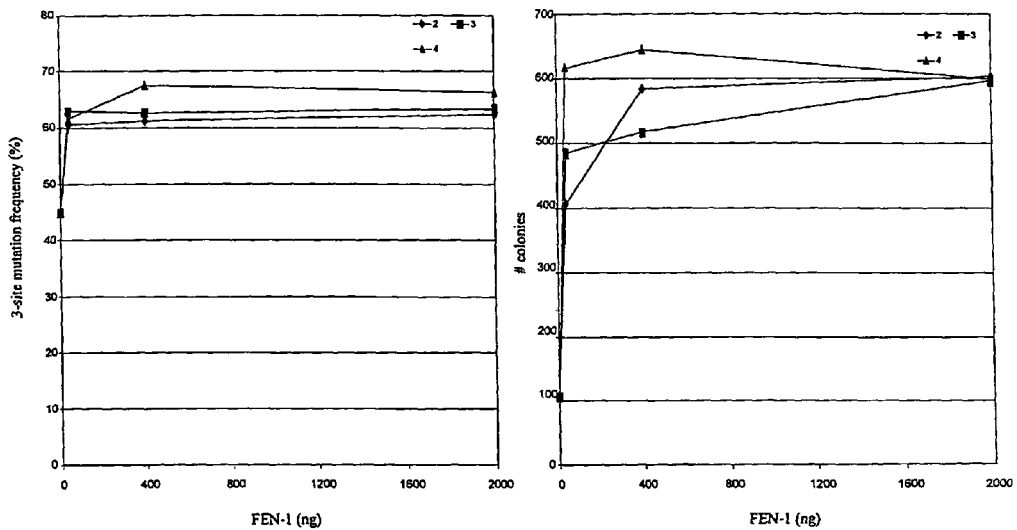
Figure 12

MULTI-SITE MUTAGENESIS

RELATED APPLICATION

The present application claims priority to U.S. provisional application U.S. Ser. No. 60/307,927, filed Jul. 26, 2001.

FIELD OF THE INVENTION

The invention relates generally to polynucleotide site-directed mutagenesis, more particularly, to compositions and methods for introducing multiple mutations into a target polynucleotide.

BACKGROUND OF THE INVENTION

An approach in molecular biology to elucidate structure/function relationships of a polypeptide involves the introduction of specific mutations in cloned genes for the analysis of phenotypes (Shortle, D., J. Biol. Chem. 264, 5315-5318, 1989). This reverse-genetic approach, employing site-directed mutagenesis, has facilitated the elucidation of structure-function relationships for a large number of genes. Such methods have also been successfully used to introduce desired characteristics into gene products for use in research and its applications. In some instances, such experiments have revealed intricacies of functional organization that were not apparent from the primary sequence or expression patterns (Matthews, B., Biochemistry 26, 6885-6887, 1987).

Methods of site-directed mutagenesis have evolved rapidly since the initial description of this concept (Smith, M., Annv. Rev. Genet. 19, 423-462, 1985). A common feature of the many methods is the use of synthetic oligonucleotides (primers) carrying the desired changes in the nucleotide sequence at the site of mutagenesis. This "mutagenic" oligonucleotide is incorporated into the sequence of interest by replacing the normal sequences with the designed oligonucleotide. This is accomplished by in vitro enzymatic DNA synthesis. A second step that requires the propagation and resolution of mutant and wild-type sequences in bacteria can greatly influence the rate of mutagenesis. Recently, the use of specially selected strains of E. coli that will allow enrichment of mutant molecules has improved the efficiency of mutagenesis (Kunkel, T. A., Proc. Natl. Acad. Sci. USA 82, 480-492, 1985).

Both the efficiency and the speed of mutagenesis have been improved by the introduction of methods based on the Polymerase Chain Reaction (PCR, Saiki, R. K. et al., Science 239, 487-491, 1986). Several methods based on PCR have been described that allow the introduction of mutations into the polynucleotide of interest. See Higuchi, R. et al., Nucl. Acids Res. 16, 7351-7367 (1988); Valette, F. et al., Nucl. Acid Res. 17, 723-733 (1989); Kadowaki, H. et al., Gene 76, 161-166 (1989); Dubau, L. et al., Nucl. Acids Res. 17, 2873 (1989).

These conventional PCR-based site-directed mutagenesis methods are limited to the mutagenesis of the sequences located at the termini of the amplified sequences.

Site-directed mutagenesis was made more efficient and quick by the QuikChange™ site-directed mutagenesis kit (Cat # 200518 and 200516, Stratagene). In the QuikChange kit, mutations are introduced with two complementary oligonucleotides (primers) that contain the desired mutation sites in the center. The mutagenic primers anneal to the plasmid template and are extended with a DNA polymerase (e.g., a Pfu DNA polymerase) in a temperature cycling reaction that employs non-strand displacing extension temperatures ($\leq 68°$ C.). The extension products are then digested with a selection enzyme (e.g., Dpn I) to selectively eliminate parental wild-type plasmid (e.g., methylated) and parental/mutant hybrids (e.g., hemi-methylated DNAs). Then the DNAs are transformed into a host cell (e.g., E. coli) to screen for the desired mutants.

However, when mutations are located too far apart (e.g., >10 bases) to be included in one mutagenic primer pair, one must perform sequential rounds of mutagenesis using a different primer set each round. Time-consuming transformation and screening steps are required before the DNA template is available for the next round of mutagenesis. Furthermore, it is often necessary to sequence the isolated recombinant clones to identify the desired mutants, which substantially increases the time between consecutive rounds of mutagenesis.

A modification of the QuikChange method was described that allows mutagenesis of 2-3 sites (~4 hours per site) in a single day (Kim et al., Biotechniques, 2000, 28:196-198). In this procedure, multi-site mutations are produced by carrying out in vitro dam-methylation between successive rounds of QuikChange mutagenesis. Only one transformation and DNA preparation step is required. Although high mutation frequencies were achieved (89.0% for 2-site mutagenesis; 83.8% for 3-site mutagenesis), this method is extremely labor intensive and requires gel isolation of Dpn I-resistant DNA at each round.

A method for introducing multiple site-directed mutations was recently described by Sawano et al (2000, Nucleic Acids Research, 28: e28). In the Sawano procedure, point mutations are introduced at several sites simultaneously by annealing mutagenic primers to the same strand of plasmid DNA. Unlike the standard QuikChange method, only one primer is required per mutation site, and the primer contains a 5' phosphate. The mutagenic primers are extended with Pfu DNA polymerase and ligated using Taq DNA ligase (step 1). The reaction products are then digested with Dpn I to eliminate methylated parental plasmid DNA (step 2). Finally, double-stranded plasmid DNA is prepared by priming circular single-stranded molecules (mutant DNAs) with endogenous Dpn I fragments or an exogenous oligonucleotide, and performing 2 additional rounds of temperature cycling (step 3; reaction uses Pfu, DNA ligase, dNTPs, and NAD (nicotinamide adenine dinucleotide) carried over from the PCR reaction). This procedure was used to prepare a GFP double mutant (Y66W/T203Y; 76% efficiency) and a quadruple mutant (>70% efficiency when step 3 was carried out with T7 primer) (Sawano, supra). The average number of colonies recovered from 2-site mutagenesis was reported to be 48 cfus (30-72 cfus per experiment).

The Sawano procedure offers several advantages for producing multiple mutations. Since point mutations are incorporated at multiple sites simultaneously within one cycling reaction, the total time required to construct and analyze mutants is reduced. Moreover, unlike the standard QuikChange method, only one primer is required per mutation site. This not only represents a cost saving, but the use of one primer also raises the possibility of creating large insertions or random site-directed mutant libraries using degenerate primers. Typically, the last step in a protein engineering or directed evolution project is to carry out saturation mutagenesis, whereby all 20 amino acid side chains are introduced at one or more site(s) known to confer the desired phenotype (Miyazaki and Arnold., J. Mol. Evol. 49: 716-720, 1999). Site-specific random mutant libraries are then screened to identify the amino acid or combination of amino acids that provides the greatest improvement in activity. The Sawano procedure was used successfully with one degenerate primer to randomly mutate amino acid T203 of GFP. In this study, mutants containing 13 different amino acid side chains at residue 203 were identified among the 62 clones isolated.

There is a need in the art for a more efficient multi-site directed mutagenesis. There is also a need for a multi-site directed mutagenesis method that generates more transformants so that large numbers of random mutants can be screened.

Directed evolution methods use the process of natural selection to combinatorially evolve enzymes, proteins, or even entire metabolic pathways with improved properties. These methods typically begin with the infusion of diversity into a small set of parent nucleotide sequences through DNA recombination and/or mutagenesis. The resulting combinatorial DNA library then is subjected to a high-throughput selection or screening procedure, and the best variants are isolated for another round of recombination or mutagenesis. The cycles of recombination/mutagenesis, screening, and isolation continue until a protein or enzyme with the desired level of improvement is found. In the last few years success stories of directed evolution have been reported (Petrounia, I. P. & Arnold, F. H. (2000) Curr. Opin. Biotechnol. 11, 325330), ranging from many-fold improvements in industrial enzyme activity and thermostability (Schmidt-Dannert, C. & Arnold, F. H. (1999) Trends Biotechnol. 17, 135136) to the design of vaccines (Patten, P. A., Howard, R. J. & Stemmer, W. P. C. (1997) Curr. Opin. Biotechnol. 8, 724733) and viral vectors for gene delivery (Powell, S. K., Kaloss, M. A., Pinskstaff, A., McKee, R., Burimski, I., Pensiero, M., Otto, E., Stemmer, W. P. & Soong, N. W. (2000) Nat. Biotechnol. 18, 12791282.

DNA shuffling (Stemmer, W. P. C. (1994) Proc. Natl. Acad. Sci. USA 91, 1074710751), along with its variants (Coco et al (2001) Nature Biotechnology 19:354; Moore et al. (2001) Proc Natl Acad Sci USA. 98:3226-31; Whalen et al. (2001) Curr Opin Mol Ther. 3:31-6), is one of the earliest and most commonly used DNA recombination protocols. It consists of random fragmentation of parent nucleotide sequences with DNase I and subsequent fragment reassembly through primerless PCR. Library diversity is generated during reassembly when two fragments originating from different parent sequences anneal and subsequently extend. This gives rise to a crossover, the junction point in a reassembled sequence where a template switch takes place from one parent sequence to another.

DNA shuffling techniques are also disclosed in U.S. Pat. Nos. 6,180,406; 6,132,970; 5,965,408; 6,165,793, 6,117,679; publications WO01/29211 and WO/0129212, all of which incorporated by references.

The key advantage of DNA shuffling is that many parent sequences can be recombined simultaneously (i.e., family DNA shuffling; Crameri, A., Raillard, S., Bermudez, E. & Stemmer, W. P. C. (1998) Nature (London) 391, 288291), generating multiple crossovers per reassembled sequence.

In the Stemmer ("sexual PCR" gene shuffling, e.g., in U.S. Pat. Nos. 6,180,406; 6,165,793; 6,132,970) method, the pool of parental genes is digested with DNase I to generate random, double-stranded DNA fragments. The fragments are size fractionated to select the smallest fragments (<50 bases), thereby maximizing the probability of multiple recombination events (and increasing diversity). The fragments are randomly assembled by cross-priming during a PCR reaction carried out in the absence of exogenous primers. Finally, the diversified products are PCR amplified using terminal primers.

WO01/29212 publication discloses a different method for DNA shuffling. In this method, single-stranded DNA, generated from a pool of parental genes, is digested with DNase I and then size fractionated. The fragments are then assembled by annealing to a "scaffold" with the following properties: 1) its DNA sequence is related—but not identical to those used to prepare DNase fragments (eliminates bias due to hybridization of fragments to their own parent); 2) it is single-stranded; 3) it is prepared with deoxyuracil to allow selective removal later in the procedure. After the fragments anneal to the scaffold (in the absence of polymerase), the duplexes are treated with Taq DNA polymerase (to trim 5' flaps), followed by Pfu DNA polymerase (to fill in gaps) and Taq DNA ligase (to ligate fragments together). The duplexes are then treated with uracil DNA glycosylase to selectively eliminate the scaffold, and the diversified products are then amplified by PCR.

There is a need in the art for generating a large number of recombinant DNA and subsequent transformants from DNA shuffling so that the chance of screening for a polypeptide product with a desired activity can be increased. There is also a need for a quicker and a simplified method for conducting DNA shuffling.

BRIEF DESCRIPTION OF DRAWINGS

FIG. 2. lacZ portion of pWS721 (SEQ ID NO: 20). The DNA sequence shown is the pWS II SK(–) β-gal anti-coding strand. To construct pWS (QuikChange kit control), the *P. furiosus* alkaline phosphatase gene (1.6 kb) was cloned into the Ssp I site, which eliminates pBS sequences 2850-442. To construct pWS721, stop codon mutations were added to pWS using H mutant and K mutant primers. The 3 stop codons in the lacZ portion of pWS721 are shown in bold type, while start and stop codons are shown in italics. The positions of the mutagenic primers QC (1,2), H (1,2), and K (1,2) are underlined.

SUMMARY OF THE INVENTION

Figure 1:
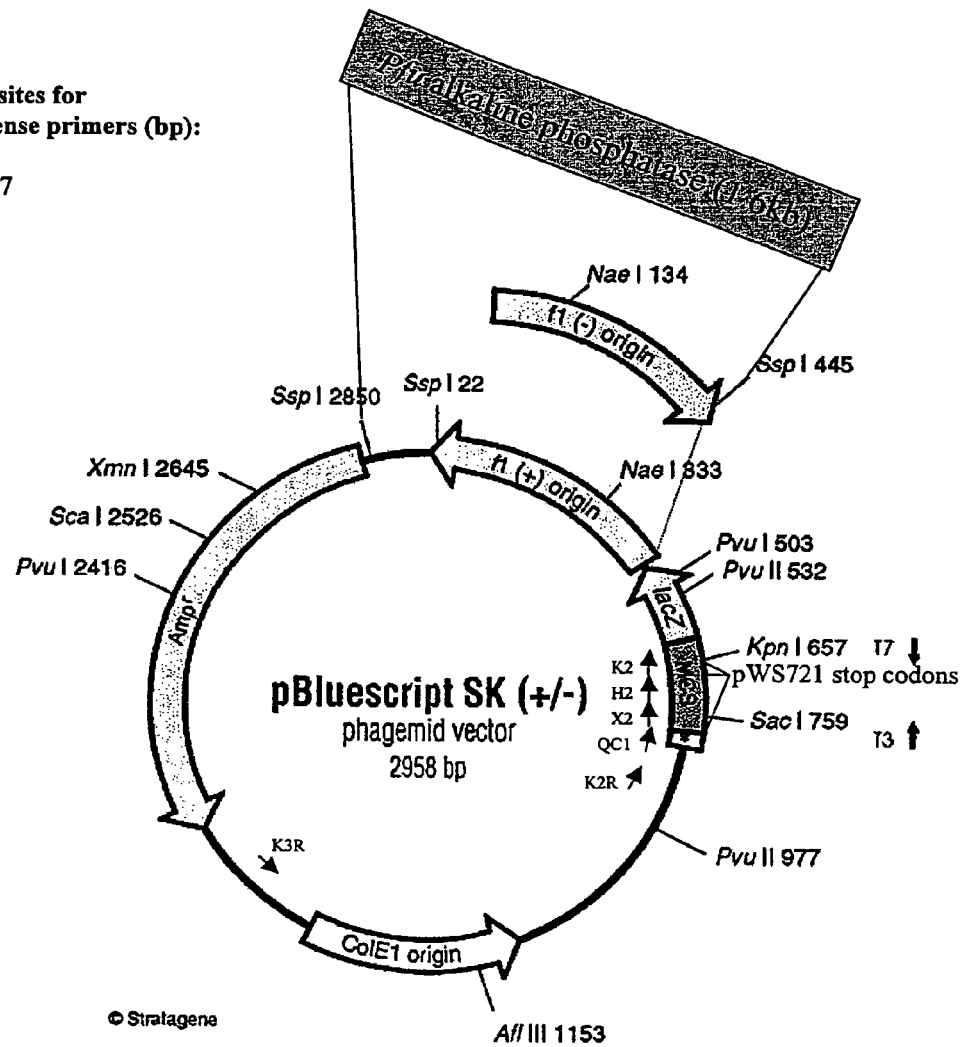
FIG. 1. Location of QuikChange Multiple Mutation mutagenic (sense) primers in pWS and its derivatives.

The present invention is directed to improved compositions and methods for multi-site directed mutagenesis and DNA shuffling. In particular, the invention relates to an improved method using a Flap endonuclease and optimized cycling conditions. The present method provides high mutation frequencies and large numbers of transformants, which are especially important for constructing random mutant libraries using degenerate primers and for DNA shuffling.

In one embodiment, the composition for introducing two or more mutations to a target DNA molecule in an amplification reaction comprises a DNA polymerase, a DNA ligase and a flap endonuclease.

In another embodiment, the composition for introducing two or more mutations to a target DNA molecule in an amplification reaction comprises a DNA polymerase, a DNA ligase, a flap endonuclease and a selection enzyme.

In yet another embodiment, the composition for introducing two or more mutations to a target DNA molecule in an amplification reaction comprises a DNA polymerase, a DNA ligase, a flap endonuclease, a selection enzyme, and a host cell for transformation.

Preferably, the DNA polymerase in the composition is a thermostable DNA polymerase.

More preferably, the DNA polymerase is a thermostable DNA polymerase selected from the group consisting of: Taq DNA polymerase, Pfu DNA polymerase, Tma DNA polymerase, Tli DNA polymerase, KOD DNA polymerase, JDF-3 DNA polymerase, PGB-D DNA polymerase, Tgo DNA polymerase and *Pyrolobus furmarius* DNA polymerase.

Yet more preferably, the Pfu-DNA polymerase is a Pfu-Turbo DNA polymerase.

Preferably, the DNA ligase in the composition is a thermostable DNA ligase.

More preferably, the thermostable DNA ligase is selected from the group consisting of: Pfu DNA ligase, Tth DNA ligase, Taq DNA ligase *Thermus filiformis* ligase, *Rhodothermus marinus* DNA ligase, *Thermus scotoductus* DNA ligase and *Bacillus stearothermophilus* DNA ligase.

The composition may further comprise NAD.

Preferably, the NAD concentration is from 0.02 mM to 0.2 mM per reaction.

More preferably, the NAD concentration is 0.1 mM per reaction.

The composition may further comprise ATP.

Preferably, in the composition, the flap endonuclease is a thermostable flap endonuclease.

More preferably, the thermostable endonuclease is selected from the group consisting of: FEN-1, RecJ, Dna2 and an exonuclease or polymerase deficient Taq DNA polymerase.

In a preferred embodiment of the invention, the composition for introducing two or more mutations to a target DNA molecule comprises Pfu DNA polymerase, Taq DNA ligase, and FEN-1.

Preferably, the Pfu DNA polymerase has a concentration of from 1.25 U to 2.5 U per 25 µl reaction, the Taq DNA ligase has a concentration of from 10 U to 20 U per 25 µl reaction, and the FEN-1 has a concentration of 400 ng to 4 µg per 25 µl reaction.

The composition may further comprise 0.01 mM to 0.2 mM NAD per reaction.

A preferred composition of the invention comprises 2.5 U Pfu DNA polymerase, 15 U Taq DNA ligase, 400 ng FEN and 0.1 mM NAD per 25 µl reaction.

All of the composition may further comprise a restriction endonuclease as a selection enzyme.

Preferably, the restriction endonuclease is methylation-dependent.

Also preferably, the methylation-dependent restriction endonuclease is selected from the group consisting of: DpnI, Nan II, NmuD I, and NmuE I All of the composition may further comprise a polymerase enhancing factor.

All of the composition may further comprise DMSO.

All of the composition may further comprise *E. coli* as a host cell for transformation.

All of the composition may further comprise at least one primer.

In one embodiment, the primer is a degenerate primer.

The present invention also provides a kit for each of the composition and packaging means therefor.

The present invention provides a method for introducing two or more mutations to a target DNA molecule, the method comprising:

a) annealing one or more primers to the same strand of said DNA molecule, wherein each said primer comprises at least one mutation site with respect to said DNA molecule;

b) synthesizing by means of an amplification reaction a mutagenized single strand of DNA comprising said primers in the presence of a DNA polymerase, a DNA ligase and a flap endonuclease; and c) digesting the non-mutagenized strands of said DNA molecule with a selection enzyme to produce a DNA product.

The invention also provides a method for introducing two or more mutations to a target DNA molecule, the method comprising:

a) annealing one or more primers to the same strand of said DNA molecule, wherein each said primer comprises at least one mutation site with respect to said DNA molecule;

b) synthesizing by means of an amplification reaction a mutagenized single strand DNA comprising said primers in the presence of a DNA polymerase, a DNA ligase and a flap endonuclease;

c) digesting the non-mutagenized strands of said DNA molecule with a selection enzyme; and d) transforming a host cell with DNA product in c).

The present invention further provides a method for introducing two or more mutations to a target DNA molecule, the method comprising:

a) annealing one or more primers to the same strand of said DNA molecule, wherein each said primer comprises at least one mutation site with respect to said DNA molecule;

b) synthesizing by means of an amplification reaction a mutagenized single strand DNA comprising said primers in the presence of a DNA polymerase, a DNA ligase and a flap endonuclease;

c) digesting the non-mutagenized strands of said DNA molecule with a selection enzyme;

d) generating a double-stranded mutagenized DNA intermediate; and e) transforming a host cell with said double-stranded mutagenized DNA intermediate.

The invention provides yet another method for DNA shuffling comprising:

a) fragmenting one or more target polynucleotides into polynucleotide fragments;

b) providing said polynucleotide fragments in an amplification reaction in the presence of a DNA polymerase, a polynucleotide template, a DNA ligase and a flap endonuclease to produce an amplified product; and c) transforming a host cell with the product from said amplification reaction.

The invention provides a method for DNA shuffling comprising:

a) fragmenting one or more double-stranded target polynucleotides into polynucleotide fragments;

b) providing said polynucleotide fragments in an amplification reaction in the presence of a DNA polymerase, a polynucleotide template, a DNA ligase and an endonuclease to produce an amplified product; and c) transforming a host cell with the product from the amplification reaction.

Preferably, the endonuclease is selected from a flap endonuclease or a DNA polymerase deficient in 5'-3' exonuclease activity or a DNA polymerase deficient in DNA polymerase activity.

More preferably, the DNA polymerase deficient in 5'-3' exonuclease activity or a DNA polymerase deficient in DNA polymerase activity is selected from the group consisting of Taq DNA polymerase, Tth DNA polymerase, and Tma DNA polymerase.

In one embodiment, the method further comprises selecting a subpopulation of said polynucleotide fragments after step a).

Preferably, in all method, the DNA polymerase is a thermostable DNA polymerase.

More preferably, the thermostable DNA polymerase is selected from the group consisting of: Taq DNA polymerase, Pfu DNA polymerase, Tma DNA polymerase, Tli DNA polymerase, KOD DNA polymerase, JDF-3 polymerase, PGB-D DNA polymerase, Tgo DNA polymerase and *Pyrolobus furmarius* DNA polymerase.

In one embodiment, the Pfu-DNA polymerase is Pfu-Turbo DNA polymerase.

Preferably, in all method, the DNA ligase is a thermostable DNA ligase.

More preferably, the thermostable DNA ligase is selected from the group consisting of: Pfu DNA ligase, Tth DNA ligase, Taq DNA ligase, *Thermus filiformis* ligase, *Rhodothermus marinus* DNA ligase, *Thermus scotoductus* DNA ligase and *Bacillus stearothermophilus* DNA ligase.

The amplification reaction in all method may further comprise NAD.

Preferably, the NAD has a concentration of from 0.02 mM to 0.2 mM per reaction.

The amplification reaction in all method may further comprise ATP.

Preferably, the flap endonuclease use in method of the present invention is a thermostable flap endonuclease.

More preferably, the thermostable flap endonuclease is selected from the group consisting of: FEN-1, RecJ and Dna2.

The amplification reaction in a preferred embodiment comprises Pfu DNA polymerase, Taq DNA ligase, and FEN-1.

Preferably the Pfu DNA polymerase has a concentration of from 1.25 U to 2.5 U per 25 µl reaction, Taq DNA ligase has a concentration of from 10 U to 20 U per 25 µl reaction, and FEN-1 has a concentration of 400 ng to 4 µg per 25 µl reaction.

The amplification reaction in all method may further comprise NAD,

In one embodiment, the selection enzyme used in the method of the present invention is a restriction endonuclease.

Preferably, the restriction endonuclease is methylation-dependent.

More preferably, the methylation-dependent restriction endonuclease is selected from the group consisting of: DpnI, Nan II, NmuD I, and NmuE I.

In another embodiment, each primer used in the method of the present invention comprises a different mutation site with respect to said DNA molecule.

The amplification reaction in all method may further comprise a polymerase enhancing factor.

In one embodiment, the amplification reaction of the present invention is performed in the presence of DMSO.

In another embodiment, an *E. coli* cell is used in the method of the invention as a host cell for transformation.

The amplification reaction in all method may comprise 3-60 reaction cycles.

In one embodiment, the target DNA molecule is a circular plasmid DNA.

In another embodiment, the method of the present invention anneals one or more primers to a first strand of a double-stranded target DNA molecule, the method further comprising annealing one or more primers to a second strand of said double-stranded target DNA molecule.

The invention provides a method comprising
a) fragmenting one or more target polynucleotides into polynucleotide fragments;
b) providing said polynucleotide fragments in an amplification reaction in the presence of a DNA polymerase, a polynucleotide template, a DNA ligase, a flap endonuclease and at least one primer to produce an amplified product; and
c) transforming a host cell with the product from said amplification reaction.

In one embodiment, the primer of step b) is a degenerate primer.

DESCRIPTION

The present invention provides for, among other things, improved methods for multi-site mutagenesis. The improved methods described herein provide for increased number of transformants, compared to the prior art. High mutation efficiency and large number of transformants allow one to sequence only a few clones in order to identify the correct mutants. Moreover, the inclusion of FEN-1, PEF, optimized thermal cycling condictions and optimized buffer conditions provided in the present invention should also facilitate site-directed random library construction and the mutagenesis of larger (>5-kb) or more difficult templates.

The present invention also provides compositions and methods for performing DNA shuffling techniques. The compositions and methods of the present invention allow a quicker and easier screening for a recombinant DNA encoding a polypeptide with desired activity.

Definitions

As used herein, the term "polynucleotide" generally refers to any polyribonucleotide or poly-deoxyribonucleotide, which may be unmodified RNA or DNA or modified RNA or DNA. "Polynucleotide" includes, without limitation, single- and double-stranded polynucleotide. As used herein, the term "polynucleotide" also includes DNA or RNA as described above that contain one or more modified bases. Thus, DNA or RNA with backbones modified for stability or for other reasons is a "polynucleotide". The term "polynucleotide" as it is employed herein embraces such chemically, enzymatically or metabolically modified forms of polynucleotide, as well as the chemical forms of DNA and RNA characteristic of viruses and cells, including, for example, simple and complex cells. "Polynucleotide" also embraces short polynucleotide often referred to as oligonucleotide.

As used herein, "mutation" refers to an alteration in a polynucleotide sequence. A mutation according to the invention can involve substitution, insertion or deletion. A polynucleotide in which a mutation has occurred is called a "mutant". Mutation may be introduced to one or both strands of a double-stranded polynucleotide. The strand of a double-stranded polynucleotide in which a mutation has occurred is referred to as a "mutant strand"; the strand with no mutation introduced is called a "non-mutant strand". The term "mutagenesis" according to the invention refers to the introduction of mutations into a polynucleotide sequence.

Mutations are preferably introduced into a target DNA molecule using one or more mutagenic primers in an amplification reaction. During the amplification reaction, multiple copies of the strand complementary to the target DNA strand are synthesized by incorporating the mutagenic primer and extending the incorporated primer using the target strand as a template.

As used herein, the term "introducing two or more mutations to a target DNA molecule" refers to introducing the two or more mutations into the same copy of the complementary strand synthesized during the amplification reaction. In addition, "introducing two or more mutations to a target DNA molecule" may also refer to introducing one or more mutations into two or more different copies of the complementary strands synthesized during the amplification reaction. For example, when a degenerate primer comprising AAX is used where X may be G or C, one copy of the synthesized strand will have AAG, another copy of the synthesized strand will have AAC.

As used herein, "substitution" refers to a replacement of one or more nucleotides by different nucleotides. "Insertion" refers to a change in nucleotide sequence wherein one or more nucleotides have been added. "Deletion" refers to a change in nucleotide sequence wherein one or more nucleotides are removed.

As used herein, "primer" refers to a polynucleotide, i.e., a purified restriction fragment or a synthetic polynucleotide, that is capable of acting as a point of initiation of synthesis when placed under conditions in which synthesis of a primer extension product complementary to a polynucleotide strand (the "template") is induced, i.e., in the presence of nucleotides and an agent for polymerization such as DNA polymerase and at a suitable temperature and pH.

The term "mutagenic primer" refers to a polynucleotide primer used in an amplification reaction, wherein the primer does not precisely match the target hybridization sequence (e.g., the sequence of a target DNA molecule). The mismatched nucleotides in the mutagenic primer are referred to as "mutation site" or "site" with respect to the target sequence (e.g., the sequence of a target DNA molecule). Thus, during the amplification reaction, the mismatched nucleotides of the primer are incorporated into the amplified product thereby resulting in the synthesis of a mutant DNA strand comprising the mutagenic primer that was used to prime synthesis mutagenizing the target sequence. Each "site" contains one or more (e.g., 2, or 3, or 4, or 5, or 10, 20, 30 or more) nucleotide mutations (e.g., substitution, insertion, or deletion).

A mutagenic primer, according to the present invention, is complementary to one strand of a target polynucleotide and contains at least 50%, and preferably at least 75%, at least 90% of the nucleotide residues capable of base pairing with a target polynucleotide molecule (e.g., a target DNA molecule).

A 'mutagenic primer' of the present invention, also refers to a "degenerate primer". As used herein, a "degenerated primer" is a primer mixture synthesized with mixed bases where there is more than one nucleotide sequence possibility for at least one codon coding for an amino acid. An amino acid is coded by three sequential nucleotides (a codon) in a polynucleotide sequence, more than one codon can encode for the same amino acid. A "degenerate primer" according to the present invention may comprise one or more degenerated codon sequences. For example, a degenerate PCR primer designed for an amino acid sequence Trp Asp Thr would be a primer with a sequence 5' TGG GAY CAN 3' (SEQ ID NO: 1) where Y is C or T, R is G or A and N is G, A, T or C. This gives a mix of maximal 8 different primers when a base mixture is provided when Y nucleotide (e.g., 50% each of C, T) and N nucleotide (e.g., 25% each of G, C, A, T) is being synthesized into the primer. A "degenerate primer" according to the present invention may also be degenerate at all nucleotide positions. That is, the primer is synthesized with random incorporation of G, C, A, T (e.g., 25% of each G, C, A, T is provided) for each nucleotide position during synthesis.

"Target polynucleotide" refers to a polynucleotide sequence, to which at least one mutation is to be introduced. In the context of a preferred application of the method according to the present invention, at least two mutations are introduced by using two mutagenic primers that are complementary to one of the two strands of a target polynucleotide (e.g., a target DNA molecule).

"Complementary" refers to the broad concept of sequence complementarity between regions of two polynucleotide strands or between two regions of the same polynucleotide strand. It is known that an adenine residue of a first polynucleotide region is capable of forming specific hydrogen bonds ("base pairing") with a residue of a second polynucleotide region which is antiparallel to the first region if the residue is thymine or uracil. Similarly, it is known that a cytosine residue of a first polynucleotide strand is capable of base pairing with a residue of a second polynucleotide strand which is antiparallel to the first strand if the residue is guanine. A first region of a polynucleotide is complementary to a second region of the same or a different polynucleotide if, when the two regions are arranged in an antiparallel fashion, at least one nucleotide residue of the first region is capable of base pairing with a residue of the second region. A first polynucleotide that is 100% complementary to a second polynucleotide forms base pair at every nucleotide position. A first polynucleotide that is not 100% complementary (e.g., 90%, or 80% or 70% complementary) contains mismatched nucleotides at one or more nucleotide positions.

As used herein, "annealing" refers to the formation of a double-stranded polynucleotide between two separate single strands sufficient to prime DNA synthesis in an amplification reaction. "Annealing" occurs through complementary base pairing between the two separated strands, which are at least 50% or more (e.g., 60%, 70%, 80%, 90%, 95% or more) complementary to each other. In the present invention, "annealing" occurs between a mutagenic primer and a target DNA molecule, and/or between a non-mutant DNA strand fragment and a mutant DNA strand.

As used herein, the term "DNA shuffling" indicates recombination between homologous but non-identical sequences.

The term "homologous" or "homeologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later. Preferably the region of identity (length of perfectly complementary base pairs) is greater than about 5 bp, more preferably the region of identity is greater than 10 bp.

The term "heterologous" means that one single-stranded nucleic acid sequence is unable to hybridize to another single-stranded nucleic acid sequence or its complement. Thus areas of heterology means that nucleic acid fragments or polynucleotides have areas or regions in the sequence which are unable to hybridize to another nucleic acid or polynucleotide. Such regions or areas are, for example, areas of mutations.

The term "population" as used herein means a collection polynucleotides with difference sequences. A "population" may be a collection of completely unrelated polynucleotides (i.e., with less than 40% sequence homology or unrelated structures or functions), or it may be a collection of polynucleotides which belong to the same family (i.e. are related in their structure or function) but which differ in their sequence (i.e. are not identical, but may have at least 60%, or 70%, or at least 80%, or 90% sequence identity) and hence are not identical in their biological activity. A "subpopulation" refers to a collection of fragmented polynucleotide population. A "subpopulation" according to the invention, has a common length range. Preferably, the length range of a subpopulation is from 10-100 base pairs, more preferably from 20 to 500 base pairs.

As used herein, "amplification" refers to any in vitro method for synthesizing one or both strands of a polynucleotide template sequence (e.g., a target DNA molecule) with the use of a polymerase. Polynucleotide amplification results in the incorporation of nucleotides into a polynucleotide (e.g., DNA) molecule or primer thereby forming a new polynucleotide molecule complementary to the polynucleotide template. The formed polynucleotide molecule and its template can be used as templates to synthesize additional polynucleotide molecules. As used herein, one amplification reaction may consist of many cycles of polynucleotide synthesis. Amplification reactions include the polymerase chain reaction (PCR, Mullis and Faloona, 1987, Methods Enzymol., 155:335, hereby incorporated as reference), ligase chain reaction (LCR), polynucleotide sequence based amplification (NASBA, Cangene, Mississauga, Ontario), Q-Beta Replicase reaction, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993).

As used herein, "polymerase chain reaction" or "PCR" refers to an in vitro method for amplifying a specific polynucleotide template sequence. The PCR reaction involves a repetitive series of temperature cycles and is typically performed in a volume of 50-100 µl. The reaction mix comprises dNTPs (each of the four deoxynucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule.

As used herein, an "amplified product" or an "amplified polynucleotide product" refers to the double strand and/or single strand polynucleotide population generated during or at the end of an amplification reaction. The amplified product contains the original polynucleotide template and polynucleotide synthesized by DNA polymerase using the polynucleotide template during the amplification reaction. The amplified product, according to the invention, contains mutations to the original polynucleotide template sequence due to the incorporation of mutagenic primers in the amplification reaction.

As used herein, "polynucleotide polymerase" refers to an enzyme that catalyzes the polymerization of nucleotide. Generally, the enzyme will initiate synthesis at the 3'-end of the primer annealed to a polynucleotide template sequence, and will proceed toward the 5' end of the template strand. "DNA polymerase" catalyzes the polymerization of deoxynucleotides. Useful DNA polymerases include, but are not limited to, *Pyrococcus furiosus* (Pfu) DNA polymerase (Lundberg et al., 1991, Gene, 108:1; U.S. Pat. No. 5,556,772, incorporated herein by reference), Taq DNA polymerase, *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Polynucleotides Res, 19: 4193), *Thermotoga maritima* (Tma) DNA polymerase (Diaz and Sabino, 1998 Braz J. Med. Res, 31:1239), *Pyrococcus kodakaraensis* KOD DNA polymerase (Takagi et al., 1997, Appl. Environ. Microbiol. 63:4504, also referred to as Pfx by Invitrogen Inc.), JDF-3 DNA polymerase (Patent application WO 0132887), *Thermococcus gorgonarius* (Tgo) DNA polymerase (Miroshnichenko et al., 1998, Int. J. Syst. Bacteriol. 48, 23-29), *Pyrolobus furmarius* DNA polymerase (Invitrogen Inc.) and *Pyrococcus* GB-D (PGB-D) DNA polymerase (Juncosa-Ginesta et al., 1994, Biotechniques, 16:820, also referred to as Deep Vent DNA polymerase by New England Biolabs). The polymerase activity of any of the above enzyme can be defined by means well known in the art. One unit of DNA polymerase activity, according to the subject invention, is defined as the amount of enzyme which catalyzes the incorporation of 10 nmoles of total dNTPs into polymeric form in 30 minutes at optimal temperature (e.g., 72° C. for Pfu DNA polymerase).

The term "selection enzyme" refers to an enzyme capable of catalyzing the digestion of a polynucleotide template for mutagenesis, but not significantly digesting newly synthesized mutagenized polynucleotide strands. Selection enzymes may differentiate between template and newly synthesized polynucleotides on the basis of modifications to either the parental template polynucleotide or modifications to newly synthesized mutagenized polynucleotides. Selection enzymes suitable for use in the subject invention have the property of selectively digesting the parental target DNA molecule and heteroduplex formed between non-mutant DNA strand and the mutant DNA strand produced in the amplification reaction step. Examples of selection enzymes include restriction endonucleases.

As used herein, "endonuclease" refers to an enzyme (e.g., restriction endonuclease) that cuts polynucleotide at sites within the polynucleotide molecule. An "endonuclease" according to the invention, includes a flap endonuclease, a restriction endonuclease, and a DNA polymerase which comprises endonuclease activity (e.g., Taq DNA polymerase, Tth DAN polymerase, Tca DNA polymerase, Tbr DAN polymerase, and Tma DNA polymerase).

"Restriction endonucleases" refers to those enzymes which cut DNA by recognizing specific sequences internal to the molecule and subsequently cutting the DNA in both strands at sites either within or outside of the recognition sequence. Restriction endonucleases occur naturally in bacteria. When they are purified away from other contaminating bacterial components, restriction endonucleases can be used in the laboratory to break DNA molecules into precise fragments. Restriction endonucleases act by recognizing and binding to particular sequences of nucleotides (the "recognition sequence") along the DNA molecule. Once bound, they cleave the molecule within, or to one side of, the sequence. Different restriction endonucleases have affinity for different recognition sequences. Endonucleases with symmetrical recognition sequences generally cleave symmetrically within or adjacent to the recognition site, while those that recognize asymmetric sequences tend to cleave at a distance of from 1 to 18 nucleotides away from the recognition site. More than two hundred unique restriction endonucleases have been identified among several thousands of bacterial species that have been examined to date (See for example, Aggarwal A K., Structure and function of restriction endonucleases. Curr Opin Struct Biol. 1995 February; 5(1): 11-9; Nath K, Azzolina B A., Cleavage properties of site-specific restriction endonucleases. Gene Amplif Anal. 1981; 1:113-30).

The term "restriction site" refers to a recognition sequence that is necessary for the manifestation of the action of a restriction enzyme, and includes a site of catalytic cleavage. When an enzyme (e.g. a restriction enzyme) is said to "cleave" or "digest" a polynucleotide, it is understood to mean that the restriction enzyme catalyzes or facilitates a cleavage of a polynucleotide.

Exceptionally, there are restriction endonucleases that are capable of cleaving methylated (typically at adenine residues), but not unmethylated DNA, like the restriction endonuclease DpnI (Lacks S A., Purification and properties of the complementary endonucleases DpnI and DpnII. Methods Enzymol. 1980; 65(1):138-46, hereby incorporated by reference). Restriction endonucleases such as DpnI are therefore referred to as "methylation-dependent".

"Structure-specific nucleases" or "structure-specific enzymes" are enzymes which recognize specific secondary structures in a nucleic molecule and cleave these structures. The site of cleavage may be on either the 5' or 3' side of the cleavage structure; alternatively the site of cleavage may be between the 5' and 3' side (i.e., within or internal to) of the cleavage structure. Structure-specific nucleases, useful according to the invention, include flap endonucleases (e.g., FEN-1, see Lieber M R. The FEN-1 family of structure-specific nucleases in eukaryotic DNA replication, recombination and repair. Bioessays. 1997 March; 19(3):233-40, hereby incorporated by reference).

The term "cleavage structure" as used herein, refers to a region of a single-stranded polynucleotide substrate containing secondary structure, said region being cleavable by a cleavage enzyme, including but not limited to an enzyme. The cleavage structure is a substrate for specific cleavage by the cleavage enzyme in contrast to a polynucleotide molecule which is a substrate for non-specific cleavage by agents such as phosphodiesterases which cleave polynucleotide molecules without regard to secondary structure (i.e., no folding of the substrate is required).

As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

Thermostable enzymes are usually purified from the hyperthermophiles of archaebacteria, which are a recently discovered group of microorganisms that grow optimally at temperatures around 100° C. Many species of these extremely thermophilic bacteria-like organisms have been isolated, mainly from shallow submarine and deep sea geothermal environments. Most of the archaebacteria are strict anaerobes and depend on the reduction of elemental sulfur for growth. The "hyperthermophiles" include, but are not limited to, *Pyrodictium*, *Pyrococcus*, and *Pyrobaculum*.

As used herein, "ligating" or "ligation" refers to covalently attaching polynucleotide sequences together to form a single sequence. This is typically performed by treatment with a ligase which catalyzes the formation of a phosphodiester bond between the 5' end of one sequence and the 3' end of the other. The ligase catalyses the formation of a phosphodiester bond at the site of a single-stranded break in duplex DNA. The ligase enzyme also catalyses the covalent linkage of duplex DNA; blunt end to blunt end, or one cohesive end to another complementary cohesive end.

Useful thermostable DNA ligases according to the invention include, but are not limited to, ligases isolated from *Thermus aquaticus* (Taq), *Thermus thermophilus* (Tth), *Pyrococcus furiosus* (Pfu) *Thermus filiformis* ligase (Lee JY et al., ActaCrystallogr D. Biol. Crystallogr, 2000, 56:351-8), *Rhodothermus marinus* DNA ligase (Hoosby J N et al., 2000, Nucleic Acid Research, 28:E10), *Thermus scotoductus* DNA ligase and *Bacillus stearothermophilus* DNA ligase (Brannigan J A, 1999, Biochimica et Biophysica Acta 1432:413). See, for example Takahashi et al., J. Biol. Chem., 259:10041-10047 (1984) and U.S. Pat. No. 5,700,672 Stratagene (La Jolla, Calif.), hereby incorporated by references. All three DNA ligases are commercially available (Taq DNA ligase, New England Biolabs, Cat# M02085; Pfu DNA ligase, Stratagene, Cat # 600191; Tth DNA ligase, Stratagene, discontinued).

As used herein, a "PCR enhancing Turbo factor (Turbo factor)" or a "Polymerase Enhancing Factor" (PEF) refers to a complex or protein possessing polynucleotide polymerase enhancing activity (Hogrefe, H., Scott, B., Nielson, K., Hedden, V., Hansen, C., Cline, J., Bai, F., Amberg, J., Allen, R., Madden, M. (1997) Novel PCR enhancing factor improves performance of Pfu DNA polymerase. Strategies 10(3):93-96; and U.S. Pat. No. 6,183,997, both of which are hereby incorporated as references). PEF, useful in the present invention, comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archaebacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). PEF is commercially available from Stratagene (Cat # 600252).

As used herein, "mutation frequency" refers to the percentage of polynucleotide which has incorporated at least one mutagenic primer used in the amplification reaction. "Mutation frequency", according to the invention may be measured by DNA sequencing or by restriction endonuclease digestion if the mutagenic primer also introduces a unique restriction site into the amplified polynucleotide product.

The term "double-stranded mutagenized circular DNA intermediate" as used herein refers to double-stranded circular DNA structures formed by annealing fragments of non-mutant strand after the digestion by a methylation-dependent restriction endonuclease (e.g., DpnI) to the mutant DNA strand. This annealing and subsequent incubating in the presence of a DNA polymerase and a DNA ligase will generate a double-stranded circular DNA intermediate which comprises one mutant stand and one non-mutant strand. This double-stranded mutagenized circular DNA intermediate is replicatively competent in a host cell.

As used herein, "host cell" refers to a cell that comprises a recombinant polynucleotide molecule, typically a recombinant plasmid or other expression vector. Thus, for example, host cells can express genes that are not found within the native (non-recombinant) form of the cell. The host cell may be prokaryotic or eukaryotic, including bacterial, mammalian, yeast, aspergillus, and insect cells.

As used herein, the term "transform" refers to a process of introducing one or more exogenous DNA molecules into a host cell and/or the expression of the DNA molecules in the host cell. A host cell with one or more exogenous DNA molecules is a transformant. According to the present invention, a large number of transformants (e.g., more than 100, more than 500, more than 1,000, or more than 10,000 transformants per μg of exogenous DNA) is desired, especially for random mutagenesis.

As used herein, "plurality" means two or more, for example, three, four, five, six, seven, eight, nine, ten, or more.

Target Polynucleotide

The present invention provides compositions and methods for introducing mutations at a plurality sites of a target polynucleotide. A target polynucleotide according to the invention may vary from 10 bp to 10 kb, or 100 kb or more in length. A DNA polynucleotide according to the invention may be a cDNA or a genomic DNA or a recombinant DNA. For example, an amplified or assembled DNA may be inserted into a suitable DNA vector, such as a bacterial plasmid or a viral vector, and the vector can be used to transform or transfect a suitable host cell.

Preferably, the target polynucleotide used in the present invention is a purified polynucleotide. By "purified", it means a naturally occurring polynucleotide sequence has been removed from its normal cellular (e.g., chromosomal) environment or a polynucleotide is synthesized in a non-natural environment (e.g., artificially synthesized).

In a preferred embodiment, a double-stranded circular DNA is used as the target polynucleotide. In a more preferred embodiment, a DNA plasmid is used as the target polynucleotide.

A person of ordinary skill in the art may readily modify the procedure so as to provide for site directed mutagenesis of circular single-stranded DNAs. In the case of a single-stranded circular DNA molecule for mutagenesis, all mutagenic primers are annealed to the same target DNA strand.

Mutagenic Primers

The mutagenic primer is preferably single-stranded for maximum efficiency in amplification but may alternatively be double-stranded. If double stranded, the primer may need to be treated to separate its strands before being used to prepare extension products. A primer must be sufficiently long to prime the synthesis of extension products in the presence of the agent for polymerization. The length of a primer depends on many factors, including application, temperature to be employed, template, reaction conditions, other reagents, and source of primers, for example, depending on the complexity of the target sequence. The mutagenic primer may be a polynucleotide and various analogs thereof. Such analogs may be base analogs and/or backbone analogs, e.g., phosphorothioates, phosphonates, and the like.

Techniques for the synthesis of primers, e.g., through phosphoramidite chemistry, are well known to the person ordinary skilled in the art and are described, among other places, in Oligonucleotides and Analogues: A Practical Approach, ed. Eckstein, IRL Press, Oxford (1992). Preferably, the primers used in the present invention are DNA molecules.

The mutagenic primers are about 20 to 50 bases in length, more preferably about 25 to 45 bases in length. However, in certain embodiments of the invention, it may be necessary to use mutagenic primers that are less than 20 bases or greater than 50 bases in length so as to obtain the mutagenesis result desired. The different mutagenic primers used in the same application may be of the same or different lengths; however, in a preferred embodiment of the invention the first and second mutagenic primers are about the same length, for example, with less than 20, preferably less than 10 bases difference in length.

The mutagenic primers may contain one or more mutation sites, i.e., mismatch locations with respect to the target DNA sequence to be mutagenized. The mutagenic site (or sites) may be used to introduce a variety of mutation types into the DNA sequence for mutagenesis. Such mutations include substitutions, insertions, and deletions. The principle of site-directed mutagenesis with single oligonucleotide primers is well known to the person of ordinary skill in the art, and can be found, for example, in Sambrook et al., Molecular Cloning: A Laboratory Manual, Second Edition, Cold Spring, Cold Spring Harbor, N.Y. (1989) and Wu et al., Recombinant DNA Methodology, Academic Press, San Diego, Calif. (1989). This information may be used to design the mutagenic sites in the mutagenic primers employed in the subject methods.

In a preferred embodiment, each mutagenic primer contains one mutation site. Preferably, the mutagenic sites are flanked by about 10-15 bases of correct, i.e., non-mutated, sequence so as to provide for the annealing of the primer to the template DNA strands for mutagenesis.

In another preferred embodiment, one or more degenerate primers are used to generate random mutations at one or more sites.

In preferred embodiments of subject methods, the GC content of mutagenic primers is at least 40%, so as to increase the stability of the annealed primers. Preferably, the mutagenic primers are selected so as to terminate in one or more G or C bases.

The mutagenic primers for use in the subject invention may be 5' phosphorylated. 5' phosphorylation may be achieved by a number of methods well known to a person of ordinary skill in the art, e.g., T-4 polynucleotide kinase treatment. After phosphorylation, the phosphorylated primers must be purified prior to use in the methods of the invention so as to remove contaminants that may interfere with the mutagenesis procedure. Preferred purification methods are fast polynucleotide liquid chromatography (FPLC) or polyacrylamide gel electrophoresis; however, other purification methods may be used. Alternatively, 5' phosphates are added synthetically, i.e., during primer synthesis.

Amplification Reaction

In the present invention, an in vitro amplification reaction is performed to introduce mutations to a target polynucleotide using one or more mutagenic primers.

Typically, the amplification reaction (e.g., PCR reaction) comprises providing a set of polynucleotide primers wherein a first primer contains a sequence complementary to a region in one strand of the polynucleotide template sequence and primes the synthesis of a complementary DNA strand, and a second primer contains a sequence complementary to a region in a second strand of the target polynucleotide sequence and primes the synthesis of a complementary DNA strand, and amplifying the polynucleotide template sequence. One or both primers used in may contain mutations.

A preferred amplification reaction, according to the present invention, however, comprises one or more mutagenic primers that are complementary to the same strand of the polynucleotide template. After the primers are annealed, synthesis of the mutant strand proceeds so as to produce a double stranded circular DNA molecule comprising a mutant DNA strand and the parental single-stranded template. Sequential annealing and synthesis reactions will use the parent strand and produce excess amount of mutant strand.

Another preferred embodiment of the present invention comprises one or more primers complementary to each strand of the polynucleotide template are included in the same amplification reaction.

The amplification reaction may be performed in repeated cycles, for example, as in polymerase chain reaction. The exact parameter of each portion of a cycle of the amplification reaction used may vary in accordance with factors such as the DNA polymerase used, the GC content of the primers, DNA concentration, etc. Cycle parameters of concern include the time of each portion of the cycle (denaturation, annealing, synthesis) and temperature at which each portion of the cycle takes place. A person of ordinary skill in the art may obtain guidance in optimizing the parameters of the amplification reaction step for individual experiments can be found in publications describing PCR. The synthesis phase of the amplification reactions used in the subject mutagenesis methods should proceed for a length of time sufficient to produce mutant DNA strands equivalent in length to the non-mutant strand (excluding insertions or deletions in the mutagenic primers) to the DNA molecule for mutagenesis.

The amplification reaction, i.e., the synthesis reaction, may be catalyzed by a thermostable or non-thermostable polymerase enzyme. Polymerases for use in the amplification reactions of the subject methods have the property of not displacing the mutagenic primers that are annealed to the template, thereby producing a mutant DNA strand of essentially the same length as the template from which the newly synthesized strand was derived. Preferably, the polymerase used is a thermostable polymerase. The polymerase used may be isolated from naturally occurring cells or may be produced by recombinant DNA technology.

Amplification reactions as employed in the methods of the invention may be carried out with a wide range number of amplification cycles required to produce the desired quantity of mutant DNA strands. Preferably the number of cycles in the amplification reaction step is 10-60 cycles, more preferably 20 to 40 cycles are performed, and even more preferably the number of cycles is between 25 and 35. The preferred embodiment of cycles will vary in accordance with the number of mutations sought to be introduced into the DNA molecule for mutagenesis. Generally, the optimum number of reaction cycles will increase with the complexity of mutations to be introduced into the DNA molecule for mutagenesis. The use of a large number of amplification cycles is troublesome because of the introduction of unwanted secondary mutations in the amplified sequences, i.e., mutations other than the intended site-directed mutagenesis target.

The subject methods of site-directed mutagenesis enable the use of a comparatively small number of amplification steps because relatively large amounts of template may be used without producing an unacceptably high background of unmutagenized DNA molecules. The digestion step performed by the selection enzyme serves to lower the background of unmutagenized DNA molecules. When a low, e.g., 5-10, number of amplification cycles are used in the amplification mutagenesis reaction, the amount of template DNA molecule for mutagenesis should be increased so that a sufficient amount of mutagenized product is produced.

DNA Polymerase

Preferred DNA polymerases of the present invention are preferred to have an error rate of less than 8 per $10^6$ base pairs.

The use of Pfu DNA polymerase (Stratagene), a DNA polymerase naturally produced by the thermophilic archaea *Pyrococcus furiosus* is particularly preferred for use in the amplification reaction steps of the claimed invention. Pfu DNA polymerase is exceptionally effective in producing mutant DNA strands of the appropriate length for formation of the desired double-stranded mutant DNA intermediates when desired. When Pfu DNA polymerase is used to catalyze the amplification reaction, the synthesis phase of the amplification reaction optimally occurs with a temperature range of 60° C.-68° C.; higher temperatures will result in the unwanted effect of mutagenic primer displacement.

Examples of other enzymes that may be used in amplification include, but are not limited to, *Thermus thermophilus* (Tth) DNA polymerase (Myers and Gelfand 1991, supra), *Bacillus stearothermophilus* DNA polymerase (Stenesh and McGowan, 1977, supra), *Thermococcus litoralis* (Tli) DNA polymerase (also referred to as Vent DNA polymerase, Cariello et al., 1991, supra), *Thermotoga maritima* (Tma) DNA polymerase (Diaz and Sabino, 1998 supra), *Pyrococcus kodakaraensis* KOD DNA polymerase (Takagi et al., 1997, supra), JDF-3 DNA polymerase (Patent application WO 0132887), *Thermococcus gorgonarius* (Tgo) DNA polymerase (Miroshnichenko et al., supra, *Pyrolobus furmarius* DNA polymerase (Invitrogen Inc.) and *Pyrococcus* GB-D (PGB-D) DNA polymerase (Juncosa-Ginesta et al., 1994, supra), Taq DNA polymerase (Stratagene), Moloney Murine Leukemia Virus reverse transcriptase, and the like. Amplification reaction buffer may be employed specifically for each enzyme according to methods well known in the art.

When the DNA molecule for mutagenesis is relatively long, it may be desirable to use a mixture of thermostable DNA polymerase. A description of how to amplify long regions of DNA using these polymerase mixtures can be found, among other places, in U.S. Pat. No. 5,436,149, Cheng et al., Proc. Natl. Aca. Sci. USA 91:5695-9 (1994), and Barnes Proc. Natl. Aca. Sci. USA 91:2216-2220 (1994). In order to determine whether or not a given polymerase (or multiple polymerase composition) is suitable for use in catalyzing the synthesis step of the amplification reaction (under a given set of conditions), a simple assay using primers and circular template may be performed so as to determine if primer displacement occurs. Primer displacement may readily be detected by performing the gel electrophoresis analysis of the assay mixture. The extension temperature or reaction conditions may be modified as necessary to eliminate or minimize strand displacement.

Polymerase Enhancing Factor

Proteins with PCR enhancing activity may be used in the amplification reaction to facilitate the amplification of long and complex mutant strand. Polymerase enhancing factors (PEFs) can be produced from a bacterial or an archeabacterial source. PEFs can be polymerase enhancing activity mixtures of one or more such proteins, protein complexes containing one or more such proteins, or extracts containing one or more of such proteins, mixtures or complexes. The Pfu P45 and P50 proteins are illustrative of PEF proteins P45 and P50, which exhibit an apparent molecular weight of approximately 45 kD and 50 kD. These two proteins are predominant components of a PEF complex derivable from *Pyrococcus furiosus* (Pfu) as described by U.S. Pat. No. 6,183,997 (hereby incorporated by reference).

In a preferred embodiment, a Pfu and P45 mixture, Pfu Turbo DNA polymerase is used to carry out the amplification reaction.

Flap Endonuclease

Flap endonuclease are an emerging family of structure-specific endonucleases that are involved in DNA replication and repair, which are critical for maintaining genome stability. These enzymes, typified by flap endonuclease-1 (FEN-1), are required for the removal of RNA primers during lagging-strand DNA synthesis and the damaged DNA fragments in various DNA-repair pathways (Kaiser et al., 1999. J. Biol. Chem. 274: 21387-94; Hosfield et al., 1998, J. Biol. Chem., 273: 27154-61; Hosfield et al., 1998, Cell 95: 135-146). To carry out these biologically essential enzymatic transformations, these nucleases must be able to cleave RNA and DNA, regardless of sequence; however, indiscriminate cleavage of substrate would be lethal to the cell. To circumvent this apparent paradox, structure-specific endonucleases recognize their substrates using a structure-based recognition mechanism, rather than a mechanism based on the chemical signatures of the constituent DNA bases.

FEN-1 is a structure-specific endonuclease that cleaves 5' flaps (Kaiser et al., supra; Hosfield et al., supra). FEN-1 plays a key role in vivo in processing Okazaki fragments during lagging strand DNA synthesis. FEN-1 is thought to remove displaced 5' strands (initiator RNA and DNA) created by DNA polymerases during displacement synthesis, to generate suitable substrates for DNA ligase. Kaiser et al have demonstrated that, after FEN-1 cleavage, upstream and downstream primers can be ligated in vitro (using T4 DNA ligase) in the absence of DNA polymerase, indicating that FEN-1 cleavage produces nicked duplexes lacking gaps (Kaiser et al., supra). FEN-1 has been cloned from a variety of sources, including *Pyrococcus furiosus*, and its structure and biochemical properties have been described (Hosfield et al., supra).

Thermostable FEN-1 endonucleases useful according to the invention include, but are not limited to, FEN-1 endonuclease purified from the "hyperthermophiles", e.g., from *M.*

*jannaschii, P. furiosus* and *P. woesei*. See U.S. Pat. No. 5,843,669, hereby incorporated by reference.

According to the methods of the present invention, the addition of FEN-1 in the amplification reaction dramatically increases the mutation frequency of the multi-site mutagenesis. 400 ng to 4000 ng of FEN-1 may be used in each amplification reaction. Preferably 400-1000 ng, more preferably, 400-600 ng of FEN-1 is used in the amplification reaction. In a preferred embodiment of the invention, 400 ng FEN-1 is used.

DNA Ligase

A DNA ligase is used in the amplification reaction to ligate the mutant fragments synthesized by extending each mutagenic primer so to form a circular mutant strand. Preferably, the DNA ligases used in the present invention are thermostable DNA ligases, for example, Taq DNA ligase, Tth DNA ligase, Pfu DNA ligase, *Thermus filiformis* ligase, *Rhodothermus marinus* DNA ligase, *Thermus scotoductus* DNA ligase and *Bacillus stearothermophilus* DNA ligase. Cofactors are required for each DNA ligase and are therefore included in each mutagenesis composition comprising a DNA ligase. Tth and Taq DNA ligase require NAD as a cofactor, while Pfu DNA ligase required ATP as a cofactor.

Tth DNA ligase and Taq DNA ligase generate similar mutation frequency, which is higher than that generated by Pfu DNA ligase. Taq DNA ligase generates a similar number of transformants compared to Tth DNA ligase.

Preferably, 1-20 U DNA ligase is used in each amplification reaction, more preferably, 2-15 U DNA ligase is used in each amplification reaction.

In a preferred embodiment, 15 U Taq DNA ligase is used in an amplification reaction. Taq DNA ligase cofactor NAD is used at a concentration of 0-1 mM, preferably between 0.02-0.2 mM, more preferably at 0.1 mM.

Selection Enzyme

By performing the digestion step, the number of transformants containing non-mutant polynucleotides is significantly reduced. The parental strand digestion step involves adding a selection enzyme to the reaction mixture after the amplification reaction has been completed. Selection enzymes may be restriction endonucleases or other enzymes that are capable of catalyzing the digestion, e.g., cleavage, of parental strands in an amplification reaction, but do not significantly digest the DNA strands newly synthesized during the amplification reaction step. Restriction endonucleases for use in the parental strand digestion step are selected so as to be able to cleave the parental strands, but not significantly cleave newly synthesized polynucleotides. The restriction endonuclease selected for use in the digestion step may (1) require a specific modification of the parental strand that is not present on the mutant DNA strands synthesized during the amplification mutagenesis reactions or (2) the restriction endonuclease selected for use in the parental strand digestion step may be unable to digest polynucleotides that have been modified in a specific way and the mutant DNA strands synthesized during amplification reaction have such a modification (and the parental template polynucleotides, i.e, the DNA molecules for mutagenesis, lack the modification).

The selection enzyme serves to digest parental strand DNA. The parental strand DNA digested may be in the form of heteroduplexes formed between parental strands and the mutant DNA strands produced in the amplification reaction step. Additionally, the parental strands digested by the selection enzyme may consist of duplexes formed between parental strands.

In order to employ a parental strand digestion step so as to reduce the parental background in site-directed mutagenesis, a polynucleotide modification step must be employed prior to the parental strand digestion step. In a polynucleotide modification step for use in the subject methods of site-directed mutagenesis, either (1) one or more of the nucleotides of the parental template polynucleotides for mutagenesis are enzymatically (or chemically) modified and the mutant DNA strands synthesized during the replication reaction, e.g., the amplification reaction, are not modified or (2) one or more of the nucleotides of the mutant DNA strands synthesized during the amplification reaction are enzymatically (or chemically) modified and the nucleotides of the parental template DNA molecules for mutagenesis are not modified. The precise modification reaction step selected for use in a given embodiment of the invention is selected in conjunction with the specific selection enzyme used in the digestion step so that the selection enzyme can digest the parental strand, i.e., the original template polynucleotides, and not significantly digest the newly synthesized mutant DNA strands.

The modifying step for use in conjunction with a parental strand digestion step may comprise the process of exposing a DNA molecule for modification to a modifying agent. The modification step may be carried out before the amplification reaction step or during the amplification reaction step. The modifying agent may be a methylase enzyme that catalyzes the methylation of a base within the polynucleotide of interest. Examples of suitable methylases for use in the invention include dam methylase, dcm methylase, Alu I methylase, and the like. The modification reaction may take place in vivo or in vitro. In vivo methylation may be conveniently achieved by propagating polynucleotides in cells, either prokaryotic or eukaryotic, that endogenously produce a suitable methylase enzyme.

In a preferred embodiment of the invention, in vivo methylation is used to carry out the modification step.

The polynucleotide modification step may also be accomplished by synthesizing polynucleotides with nucleotides comprising a modified base, e.g., 6-methyl-ATP, rather than directly modifying a polynucleotide after the polynucleotide has been completely synthesized. When the modification reaction is a methylation reaction and the selection enzyme is a restriction endonuclease that requires methylated bases for activity, the methylation step is preferably performed in vivo. When the selection enzyme is a restriction endonuclease that does not cleave its recognition sequence when the recognition sequence of the enzyme is unmethylated, the modification reaction is preferably a methylation reaction performed in vitro by a polymerase catalyzing the incorporation of methylated nucleotides into a newly synthesized polynucleotide strand. When the selection enzyme used in the digestion step is Dpn I, the modification step is preferably the methylation of adenine to produce 6-methyl adenine (dam methylase) and the methylation reaction preferably takes place in vivo by propagating the target DNA for mutagenesis as a plasmid in a suitable prokaryotic host cell.

Restriction endonucleases are preferred for use as selection enzymes in the digestion step. A preferred selection enzyme for use in the parental strand digestion step is the restriction endonuclease Dpn I, which cleaves the polynucleotide sequence GATC only when the adenine is methylated (6-methyl adenine). Other restriction endonucleases suitable for use in the parental strand digestion step include Nan II, NmuD I, and NmuE I. However, restriction endonucleases for use as selection enzymes in the digestion step do not need to be isoschizomers of Dpn I.

Various restriction enzymes are commercially available and their reaction conditions, cofactors and other requirements are used as would be known to the ordinarily skilled artisan (e.g., Stratagene; New England Biolabs). Appropriate buffers, substrate amounts, and working conditions (e.g., temperature) for particular restriction enzymes are specified by the manufacturer.

Other enzymes for use as selection enzymes include uracil N-glycosylase. Uracil deglycosylase may be used as a selection enzyme by modifying a target DNA molecule for mutagenesis to contain one or more uracil bases rather than thymidine. Uracil incorporation preferably occurs in vivo so that uracil deglycosylase may provide for the digestion of parental strands. Polynucleotides may be modified to as to contain uracil residues by a variety of methods including DNA synthesis with dUTP as a DNA precursor or the replication of DNA in a dut⁻ ung⁻ strain of $E.$ $coli.$ Polynucleotides comprising uracil bases are sensitive to deglycosylation, i.e., digestion, by uracil N-glycosylase and other enzymes with similar glycosylase activity. The use of uracil N-glycosylase is described, among other places in Kunkel, PNAS USA, 82:488-492 (1985).

Double-Stand DNA Intermediate

After the "digestion" step is completed or concurrent with the "digestion" step, i.e., the addition of the selection enzyme, an additional complementary primer or the fragments of the parent strand may be annealed to the mutant DNA strand and subject to another amplification reaction so as to produce a double-stranded mutagenized circular DNA intermediate. The formation of double-stranded mutagenized circular DNA intermediate takes place in accordance with conventional principles of nucleic acid hybridization and may be performed under a variety of conditions. Conveniently, the annealing of the parental strand fragments to the mutant DNA strand so as to form a double-stranded mutagenized circular DNA intermediate may take place simultaneously with the "digesting" step. The formation of the double-stranded circular DNA intermediates may take place in the same reaction vessel in which the "digesting" and/or the amplification reaction step take place. The process of forming double-stranded mutagenized circular DNA intermediates should proceed for a period of time sufficient to produce a convenient number of double-stranded mutagenized circular DNA intermediates to provide a convenient number of clones in the subsequent transformation steps.

Transformation and Host Cells

After the digestion step is completed with or without the formation of the double-stranded circular DNA intermediates, the mutant DNA product are subsequently used to transform a competent host cell. Transformed host cells may then be isolated as colonies. Plasmids, i.e., closed circular DNAs, corresponding to the initial DNA molecules for mutagenesis, but containing the desired site-directed mutation or mutations, may be isolated from the transformed cells.

The reaction mixture or a portion thereof, may be used to transform competent single-cell microorganism host cells. It is not necessary to perform a ligation reaction prior to transformation of the host cells. The absence of a ligation step requirement serves to reduce the time and expense required to carry out the methods of the invention as compared with conventional methods of site directed mutagenesis. The host cells may be prokaryotic or eukaryotic. Preferably the host cells are prokaryotic, more preferably, the host cells for transformation are $E.$ $coli$ cells. Techniques for preparing and transforming competent single cell microorganisms are well know to the person of ordinary skill in the art and can be found, for example, in Sambrook et al., Molecular Cloning: A Laboratory Manual Coldspring Harbor Press, Coldspring Harbor, N.Y. (1989), Harwood Protocols For Gene Analysis, Methods In Molecular Biology Vol. 31, Humana Press, Totowa, N.J. (1994), and the like. Frozen competent cells may be transformed so as to make the methods of the invention particularly convenient.

Random Mutagenesis, Large and Difficult Target Mutagenesis

Site-directed random mutagenesis uses one or more degenerate primer to introduce one or more mutations at each target mutation site.

In site-directed random mutagenesis, a large number of transformants may be required in order to generate enough mutant DNA screen for a desired phenotype. The original Sawano procedure is not theoretically applicable for random combinations of 1 primer with two degenerate (NNX) codons or 2 mutagenic primers with one degenerate (NNX) codon, both of which contain 400 different combinations of all possible amino acids at 2 positions and need to be encoded by 1024 clones with all possible combinations of all possible codons. In applications with 1 primer containing three degenerate (NNX) codons or 3 mutagenic primers with one degenerate (NNX) codon, 8000 different combinations of all possible amino acids at 3 positions may be required, which need to be encoded by 37,768 clones with all possible combinations of all possible codons. The present invention makes this application, which requires large number of transformants, feasible and more efficient. In contrast, less than 200 clones were reported for the Sawano procedure. Therefore the Sawano procedure is not capable of generating the numbers of mutants that are useful for efficient DNA random mutagenesis.

Unlike the standard QuikChange method, which employs two complementary mutagenic primers, the Multi-Site mutagenesis may use one primer per mutation site. Therefore, a person skilled in the art should be able to adapt the present Multi-Site method for use with degenerate primers and primers designed to introduce large insertions or deletions. Degenerated primers can introduce various mutations at a directed site, therefore allowing the study of structure-function relationship of a polynucleotide and its polypeptide product.

When creating insertions with the standard QuikChange method, efficiencies tend to decrease as the size of the insertion increases. Reduced efficiency has been attributed to preferential binding of the complementary mutagenic primers to each other rather that to the parental plasmid DNA template. Since only one primer is employed in the Multi-Site mutagenesis method, large insertions should be incorporated much more efficiently than with the standard QuikChange method.

DNA Shuffling

The compositions and methods of the present invention may be used for DNA shuffling. Again, the high numbers of transformants recovered in the method of present invention allows the construction and screening of random mutant libraries with $10^4$-$10^6$ members, for example 833,333 cfus may be generated per QuikChange reaction).

Techniques for DNA shuffling are disclosed in a number of references, for example, Stemmer, W. P. C., supra; Coco et al., supra; Moore et al., supra; Whalen et al., supra; U.S. Pat. Nos. 6,180,406; 6,132,970; 5,965,408; 6,165,793, 6,117,679; publications WO01/29211 and WO/0129212, all of which incorporated by references.

An error-prone DNA polymerase (e.g., Taq DNA polymerase or exo-Pfu DNA polymerase as described in U.S. Pat. No. 5,489,523) may be used for DNA shuffling to increase the mutation diversity of the DNA shuffling product.

The major advantage of the method in the present invention over the technique disclosed in patent application WO01/29212 is the lack of requirement for a single-stranded uracil-containing scaffold. Instead the present invention relies on thermal cycling to denature the template and Dpn I to selectively eliminate parental DNAs. In addition, FEN-1 ma be employed to remove 5' flap instead of Taq DNA polymerase, and PfuTurbo is used instead of Pfu to increase PCR efficiency.

Degenerate primers may also be used in DNA shuffling to further increase the diversity.

Compositions

The invention provides composition for introducing mutations to a target DNA molecule, and for DNA shuffling. At a minimum, the composition of the present invention contains a DNA polymerase, a DNA ligase and a flap endonuclease.

Preferably, the composition comprises 400 ng to 4 µg of FEN-1 for each amplification reaction.

Preferably, the composition provides the DNA polymerase at 1-5 U per 25 µl amplification reaction, more preferably at 2-4 U per 25 µl reaction.

Also preferably, the composition provides the DNA ligase at 1-20 U per 25 µl amplification reaction. In a preferred embodiment, 15 U Taq DNA ligase per 25 µl reaction is used.

Compositions of the invention may further contain one or more of the following items: individual nucleotide triphosphates, mixtures of nucleoside triphosphates (including equimolar mixtures of dATP, dTTP, dCTP and dGTP), methylases (including Dam methylase), control amplification primers, control template, a selection enzyme, bacterial strains for propagating methylated plasmids (or phage), frozen competent cells, concentrated reaction buffers, DMSO, cofactors (e.g., NAD) and the like.

Kits

Another aspect of the invention is to provide kits for performing multi-site mutagenesis and DNA shuffling. The kits of the invention provide one or more of the enzymes or other reagents for use in performing the subject methods. Kits may contain reagents in pre-measured amounts so as to ensure both precision and accuracy when performing the subject methods. Kits may also contain instructions for performing the methods of the invention. At a minimum, kits of the invention comprise a DNA polymerase (preferably Pfu DNA polymerase), a DNA ligase (preferably Taq DNA ligase) and a flap endonuclease (preferably FEN-1).

Kits of the invention may further contain one or more of the following items: individual nucleotide triphosphates, mixtures of nucleoside triphosphates (including equimolar mixtures of dATP, dTTP, dCTP and dGTP), DMSO, methylases (including Dam methylase), control amplification primers, control template, a selection enzyme, bacterial strains for propagating methylated plasmids (or phage), frozen competent cells, concentrated reaction buffers, and the like.

The terms "control template" and "control primer" as used herein refer to circular double-stranded DNA molecules and mutagenic primers, respectively that are selected to provide for easily detectable site-directed mutagenesis by the methods of the invention. For example, a control template may comprise a lac Z gene with a point mutation and the control primers may be designed to introduce a site-directed mutation that "repairs" the point mutation. As the lac Z phenotype is easily detected on indicator media, e.g., X-gal, the efficiency of the mutagenesis protocol may be easily monitored.

Preferred kits comprise a DNA polymerase, a FLAP endonuclease, a DNA ligase, concentrated reaction buffer, a selection enzyme, a nucleoside triphosphate mix of the four primary nucleoside triphosphates in equal molar amounts, frozen competent cells, DMSO, cofactors (e.g., NAD), control primers, and control templates. The DNA polymerase, DNA ligase and FEN-1 may be provided as an enzyme mixture.

An example of the preferred kit of the present invention is the QuikChange Multi Site-Directed Mutagenesis kit, which comprises Pfu Turbo DNA polymerase, Taq DNA ligase, Pfu FEN-1, dNTPs, DpnI, QuikSolution, control plasmid DNA, control primer mix, 10× reaction buffer (e.g., with NAD), β-mercaptoethonal, XL10-Gold® ultracompetent cells.

Preferably, the Pfu Turbo DNA polymerase, Taq DNA ligase and Pfu FEN-1 are provided as an enzyme blend.

EXAMPLES

Example 1

Materials and Methods

Enzymes and Reagents

The materials used in the following examples are obtained from Stratagene and other bioreagent providers as listed below.

PfuTurbo DNA polymerase (Stratagene, Cat. #600252)
Taq DNA ligase (New England BioLabs #M0208S)
Pfu FEN-1
dNTPs (Stratagene, Cat. #200415)
Dpn I (Stratagene, Cat. #500402)
QuikSolution (Stratagene, Cat. 200516)
control plasmid DNA (pWS72I)
control primer mix (QC1, K2, H2)
βME
XL 10-Gold® ultracompetent cells (Stratagene, Cat. 200314), Pfu DNA ligase (Stratagene, Cat. #600191), Tth DNA ligase (Stratagene, discontinued product; lot #123402A used here),
BSA (Stratagene, Cat. #300041).

Components for reaction buffer (e.g., Tris-HCl, KCl, $(NH_4)_2SO_4$, $MgCl_2$, and $MgSO_4$) were obtained form various reagent providers. NAD (Sigma #N1636) was prepared as a 10 mM stock solution in water and stored at −20° C. 10× reaction buffers were prepared and stored at −20° C.

Construction of Target Plasmid DNAs

Test plasmids for evaluating the QuikChange Multi-Site kit (QCMS) were constructed from pWhitescript (pWS; 4.0 kb), the standard QuikChange kit control (Table 1). pWS contains the *P. furiosus* alkaline phosphatase gene, cloned into the Ssp I 2850/445 sites of pBluescript SK, and a stop codon (TAA) mutation in the lacZ gene (792 bp) which prevents β-galactosidase synthesis (FIG. 1). For the standard QuikChange kit control, pWS is mutated with primers QC1 and QC2 to convert the stop codon to the wild type sequence (CAA). Incorporation of the desired mutation is monitored by conversion from white (lacZ) to blue (lacZ⁺) when transformants are plated on IPTG/X-gal plates.

The control DNA for the QuikChange Multi-Site kit (pWS721) was prepared by site-directed mutagenesis of pWS using a modification of the Sawano method (3). Two additional stop codons were introduced into the lacZ gene using the H mutant and K mutant primers (see Table 2). The control pWS721 plasmid contains a total of 3 stop codons in lacZ that can be converted to wild type sequences using the kit control primers QC1, K2, and H2 (FIG. 2) or the antisense primers QC2, K1, and H1. Successful mutagenesis of all 3 stop codons can be monitored by plating transformants on IPTG/X-gal plates and scoring the number of blue colonies (only three-site mutants regain β-galactosidase activity).

A second mutant plasmid (pWS72) was prepared by introducing one extra stop codon into the lacZ gene using the K mutant primer. The pWS72 test plasmid contains 2 stop codons in lacZ that can be converted to wild type sequences using either the sense QC1 and K2 primers or the antisense QC2 and K1 primers (Table 1). Successful mutagenesis of both stop codons is monitored by blue/white color screening (only double mutants regain β-galactosidase activity). A third mutant plasmid (pWS74), containing three stop codons in lacZ, was also constructed from pWS using the K mutant and X mutant primers. Conversion to wild type is carried out with sense primers QC1, K2, and X2 or antisense primers QC2, K1, and X1. pWS74 transformants were found to produce light blue colonies on IPTG/X-gal plates, which presumably reflects read through of the stop codon at position 732 (X mutant primer).

The plasmid templates used in these studies were purified using the StrataPrep Plasmid Miniprep kit (#400761).

TABLE 1

Mutagenesis systems used to test the QuikChange Multi-Site kit

| QCMS test plasmids | stop codon mutations in lacZ (bp) | loss of restriction sites (vs. pWS) | mutation primers (lacZ⁻ lacZ⁺) |
|---|---|---|---|
| pWS | 792 | | QC1/2 |
| pWS72 | 792, 656/657 | Kpn I at 657 | QC1/2, K1/2 |
| pWS74 | 792, 656/657, 732* | Kpn I at 657 and Xba I at 732 | QC1/2, K1/2, X1/2 |
| pWS721 | 792, 656/657, 689 | Kpn I at 657 and Hind III at 689 | QC1/2, K1/2, H1/2 |

β-galactosidase synthesis weakly detectable

Mutagenic Primers

Mutagenic primers were synthesized with a 5' phosphate moiety (Genset or Oligos Etc.). PAGE-purified and ethanol-precipitated oligos were tested and appeared to perform comparably.

TABLE 2

Mutagenic primers used with the QuikChange Multi-Site kit

| Name | Sequence(5'-3') | SEQ ID NO: | Tm (° C.) | sense/ antisense | function |
|---|---|---|---|---|---|
| H1 | GGT CGA CGG TAT CGA TAA GCT TGA TAT CGA | 1 | 65 | antisense | eliminates stop codon and adds |
| H2# | TCG ATA TCA AGC TTA TCG ATA CCG TCG ACC | 2 | 65 | sense | Hind III site to pWS72 |
| H mutant | GGT CGA CGG TAT CGA TTA GCT TGA TAT CGA | 3 | 65 | antisense | used to prepare pWS721; ad a stop codon and eliminates Hind III site from pWS |
| K1 | ATA GGG CGA ATT GGG TAC CGG GCC CCC CCT CGA | 4 | 80 | antisense | eliminates stop codon and adds Kpn |
| K2# | TCG AGG GGG GGC CCG GTA CCC AAT TCG CCC TAT | 5 | 80 | sense | I site to pWS72, pWS74, and pWS721 |
| K mutant | ATA GGG CGA ATT GGG TTA CGG GCC CCC CCT CGA | 6 | 79 | antisense | used to prepare pWS72 and pWS721; adds stop codon an eliminates Kpn I site from pWS |
| X1 | GGG ATC CAC TAG TTC TAG AGC GGC CGC CAC | 7 | 71 | antisense | eliminates stop codon and adds Xba |
| X2 | GTG GCG GCC GCT CTA GAA CTA GTG GAT CCC | 8 | 71 | sense | I site to pWS74 |
| X mutant | GGG ATC CAC TAG TTA TAG AGC GGC CGC CAC | 9 | 70 | antisense | used to prepare pWS74; add stop codon and eliminates Xba I site from pWS |
| QC1# | C CAT GAT TAC GCC AAG CGC GCA ATT AAC CCT CAC | 10 | 75 | sense | eliminates stop codon in pWS, |
| QC2 | GTG AGG GTT AAT TGC GCG CTT GGC GTA ATC ATG G | 11 | 75 | antisense | pWS72, pWS74, and pWS721 |
| K2R | GCT CAC TCA TTA GGT ACC CCA GGC TTT ACA | 12 | 76 | sense | introduce Kpn I sites into pWS, pWS72, and pWS721 900* |

TABLE 2-continued

Mutagenic primers used with the QuikChange Multi-Site kit

| Name | Sequence(5'-3') | SEQ ID NO: | Tm (° C.) | sense/ antisense | function |
|------|-----------------|------------|-----------|------------------|----------|
| K3R | CTG ATT AAG CAT TGG TAC CTG TCA GAC CAA G | 13 | 74 | sense | introduce Kpn I sites into pWS, pWS72, and pWS721 at 1973* |

*Restriction digestion with Kpn I produces fragments of 2.7 kb, 1.1 kb, and 243 bp when K2R and K3R are successfully incorporated into pWS, and fragments of 2.9 kb and 1.1 kb when both primers are incorporated into pWS72 and pWS721.
to be used as kit control primers with pWS721

Mutagenesis Amplification Reaction Conditions

In the examples, PCR was used to perform the mutagenesis amplification. The mutagenesis reaction mixture (25 µl) contained:
- 1× X buffer #12
- 200 µM each dNTP
- 50 ng plasmid DNA
- 100 ng each primer
- 1.25 U or 2.5 U PfuTurbo DNA polymerase
- 4 U Tth ligase (or 20 U Taq DNA ligase)
- 400 ng FEN-1

The mutagenesis control reaction (25 µl) contained:
- 1× buffer #12
- 200 µM each dNTP
- 50 ng pWS721 plasmid DNA
- 100 ng each primer (QC1, K2, H2)
- 1.25 U or 2.5 U PfuTurbo DNA polymerase
- 4 U Tth ligase (or 20 U Taq DNA ligase)
- 400 ng FEN-1

The reactions were cycled using the following conditions, optimized for the RoboCycler 40 or 96 temperature cycler: 1 cycle of 1 min at 95° C., 30 cycles of 1 min at 95° C. 1 min at 55° C., 2 min/kb at 65° C. (8 minutes used for kit control reaction).

After temperature cycling, 0.5 µl of Dpn I was added and the samples were incubated at 37° C. for 1 hour.

Transformation

XL10-Gold ultracompetent cells (100 µl) were transformed with 1.5 µl of each Dpn I-digested sample.

Blue/White Color Screening lacZ$^+$ revertants were scored by blue/white color screening. 100 µl of 10 mM IPTG (in water) and 100 µl of 2% X-gal (in DMF) were spread on LB agar plates 30 minutes prior to plating the transformations. Cultures were spread onto X-gal/IPTG plates and the plates were incubated overnight at 37° C. The number of blue colonies (lacZ$^+$ revertants of pWS, pWS72, pWS74, pWS721) and the total number of colonies were counted. Mutation frequency was determined as: # blue cfus/total # cfus.

Analysis of K3R/K2R Mutants

To monitor incorporation of the K3R and K2R primers (primers introduce Kpn I sites), 10 blue colonies were isolated and grown overnight. Plasmid DNA was purified and a sample of each clone was restriction digested with Kpn I. The digestion products were analyzed on 1% agarose gels and the percentage of clones with the correct mutation determined.

Example 2

Preliminary Optimization of Reaction Conditions

Initial optimization studies (buffer, enzyme concentrations, cycling conditions) were carried out with PfuTurbo DNA polymerase and Tth DNA ligase, in the absence of FEN-1. Reaction conditions were optimized using the test systems described in Materials and Methods. Unless noted, optimization experiments employed pWS721 and mutagenic primers QC1, K2, and H2, which convert three stop codons in the lacZ gene to wild type sequences (FIG. 2). Mutation efficiency (incorporation of all 3 mutations) is calculated by determining the percentage of clones that produce blue colonies (lacZ$^+$) on X-gal/IPTG plates. Although not done here, successful incorporation of the H and K primers can also be monitored by creation of restriction sites (Hind III and Kpn I, respectively).

NAD Concentration

Figure 3:
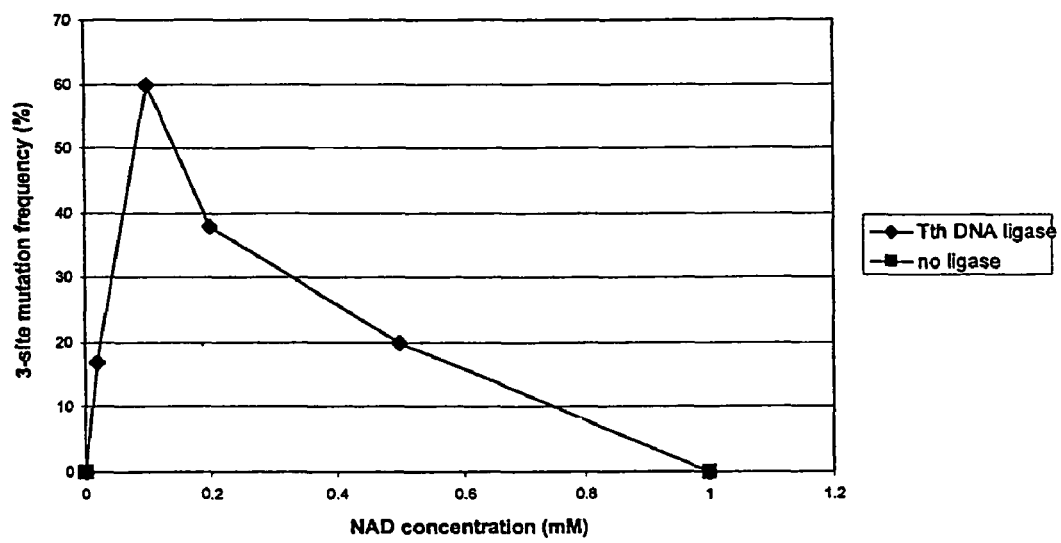
FIG. 3. Preliminary optimization of NAD concentration for the QuikChange Multi-Site Kit. Mutagenesis reactions were carried out with pWS74 and primers QC2, X1, and K1 as described in Methods except that cloned Pfu buffer, 2 U Tth DNA ligase, 18 cycles, and no FEN-1 were used.

Preliminary studies were carried out to determine the optimal concentration of NAD to employ in QuikChange Multi-Site mutagenesis. Tth and Taq DNA ligase require NAD as a co-factor, while Pfu DNA ligase employs ATP. In FIG. 3, mutagenesis reactions were carried out in cloned Pfu PCR buffer using Tth DNA ligase and varying concentrations of NAD (0-1 mM). The highest mutation efficiency (60% of clones incorporated 3 mutations) was obtained in the presence of 0.1 mM NAD (>0.02 mM and <0.2 mM).

Buffer Optimization

Initial studies were carried out to identify the best buffer to employ with Tth DNA ligase and PfuTurbo DNA polymerase. The recommended reaction buffers for PfuTurbo DNA polymerase, Tth DNA ligase, and Taq DNA ligase are listed in Table 3.

TABLE 3

Recommended enzyme reaction buffers

| Component | PfuTurbo | Tth DNA ligase | Taq DNA ligase |
|-----------|----------|----------------|----------------|
| Tris | 20 mM | 20 mM | 20 mM |
| pH | 8.8 | 7.5 | 7.6 |
| K$^+$ | 10 mM KCl | 20 mM KCl | 25 mM Kac |
| (NH$_4$)$_2$SO$_4$ | 10 mM | — | — |
| Mg$^{2+}$ | 2 mM MgSO$_4$ | 10 mM MgCl$_2$ | 10 mM MgAc |
| DTT | — | 1 mM | 10 mM |
| cofactor | — | 0.1 mM NAD | 1 mM NAD |
| stabilizers | 100 µg/ml | — | — |
| detergent | 0.1% Triton | 0.1% NP-40 | 0.1% Triton X-100 |

Figure 5:
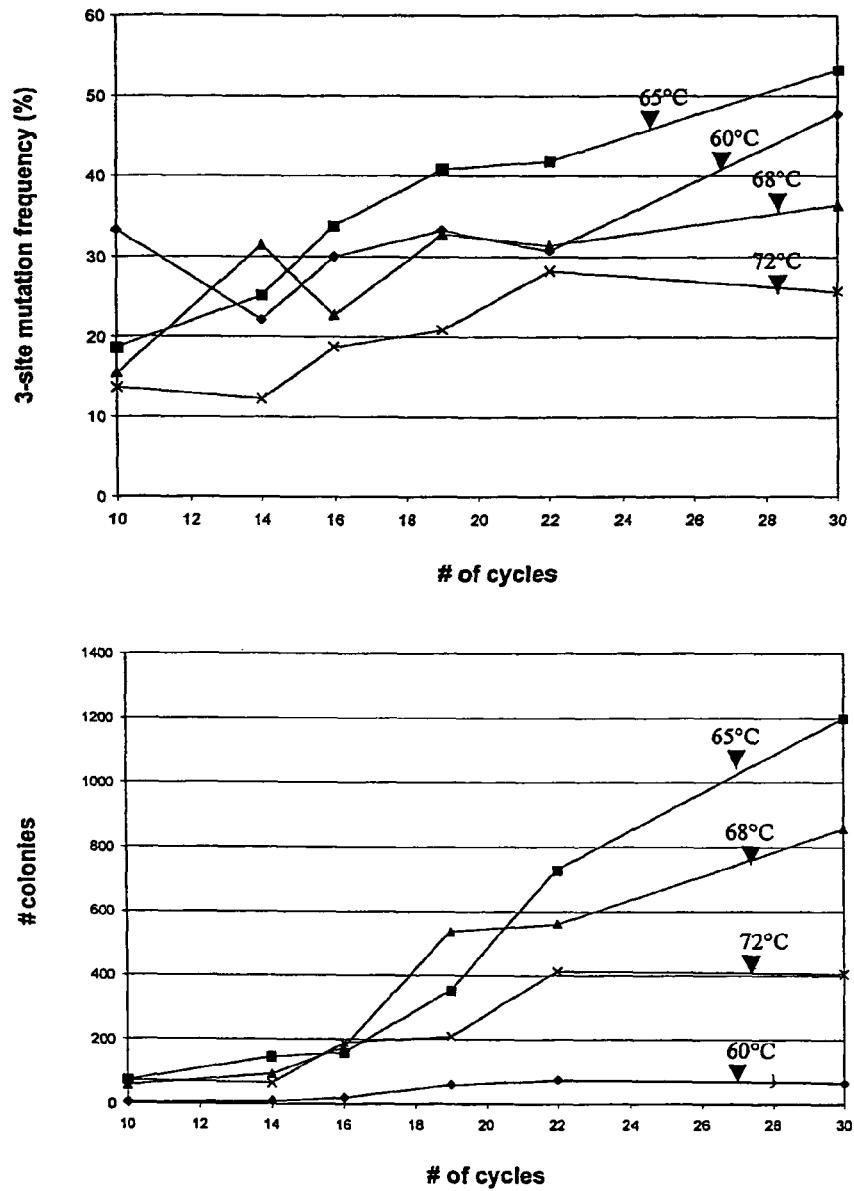
FIG. 5. Optimal cycling conditions for QuikChange Multi-Site Kit. Mutagenesis reactions were carried out with pWS721 and primers QC1, H2, and K2 using the indicated extension temperatures and number of cycles. Mutagenesis was performed as described in Methods, except that reaction buffer #2, 6 U of Tth DNA ligase, 50 ng of each primer, 100 uM each dNTPs, and no FEN-1 were used. Incorporation of all three primers was monitored by blue/white screening.

A series of related buffers were prepared and tested in the QuikChange Multi-Site mutagenesis procedure (Table 4) Each buffer contained 0.1% Triton X-100, 20 mM TrisHCl, and 100 µg/ml BSA, and differed with respect to pH or the concentrations of KCl, (NH$_4$)$_2$SO$_4$, MgSO$_4$, MgCl$_2$, DTT, and NAD. In comparisons employing buffers #1-8, as well as equal-part-mixtures of Pfu and DNA ligase buffers, optimal results were achieved using reaction buffers #1 and 2 (FIG. 5). Approximately 1000-1200 cfus were obtained after transforming with reactions carried out in buffers 1 and 2, compared to 200-950 cfus produced from reactions employing other buffers. With the exception of buffer #4, all reactions produced one-site mutation frequencies (single point mutation at 792) ranging from 77% to 95%.

the mutagenic primer around the plasmid DNA template, PfuTurbo can displace the primer and continue polymerizing through the mutation site. In addition to extension temperature requirements, the performance of the QuikChange Multi-Site method depends upon efficient intra-molecular

TABLE 4

Reaction buffers evaluated with the QuikChange Multi-Site kit

|  | 1 | 2 | 3 | 4 | 5 | 6 | 7 | 8 | 10 | 11 | 12 | 13 | 14 | 15 | 16 | 17 |
|---|---|---|---|---|---|---|---|---|---|---|---|---|---|---|---|---|
| Tris (mM) | 20 | 20 | 20 | 20 | 20 | 20 | 20 | 20 | 20 | 20 | 20 | 20 | 20 | 20 | 20 | 20 |
| pH | 8.8 | 8.8 | 8.8 | 7.5 | 8.8 | 8.8 | 8.8 | 7.5 | 8.8 | 8.8 | 8.8 | 8.8 | 8.8 | 8.8 | 8.8 | 8.8 |
| KCl (mM) | 10 | 20 | 10 | 20 | 10 | 10 | 10 | 25 | 10 | 10 | 10 | 10 | 20 | 20 | 20 | 20 |
| AmSO$_4$ (mM) | 0 | 0 | 10 | 0 | 0 | 0 | 0 | 0 | 10 | 0 | 10 | 0 | 10 | 0 | 10 | 0 |
| MgSO$_4$ (mM) | 0 | 0 | 2 | 0 | 0 | 0 | 0 | 0 | 2 | 2 | 0 | 0 | 2 | 2 | 0 | 0 |
| MgCl$_2$ (mM) | 2 | 2 | 0 | 2 | 5 | 2 | 2 | 10 | 0 | 0 | 2 | 2 | 0 | 0 | 2 | 2 |
| BSA (µg/ml) | 100 | 100 | 100 | 100 | 100 | 100 | 100 | 100 | 100 | 100 | 100 | 100 | 100 | 100 | 100 | 100 |
| TritonX-100 (%) | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| DTT (mM) | 0 | 0 | 0 | 0 | 0 | 0 | 0 | 10 | 0 | 0 | 0 | 0 | 0 | 0 | 0 | 0 |
| NAD (mM) | 0.1 | 0.1 | 0.1 | 0.1 | 0.1 | 0.5 | 0.1 | 0.3 | 0.1 | 0.1 | 0.1 | 0.1 | 0.1 | 0.1 | 0.1 | 0.1 |

Reaction Volume

Equivalent mutation efficiencies and numbers of transformants have been obtained from reactions carried out in 25 µl and 50 µl final volumes (same component concentrations; data not shown). To conserve reagents, a 25 µl reaction volume will be recommended for the QuikChange Multiple Mutations kit since only 1.5 µl is required for transformation. Temperature cycling has been performed successfully with 25 µl reaction volumes using both 600 µl and 200 µl tubes.

Cycling Conditions

QuikChange Multi-Site reactions were carried out for 10, 14, 16, 18, 22, or 30 cycles using extension temperatures of 60° C., 65° C., 68° C., or 72° C. (FIG. 5). The highest mutation efficiencies and numbers of transformants were obtained in reactions employing a 65° C. extension temperature. Presumably, 65° C. reflects an optimal balance between polymerization (increases number of transformants), melting of the mutagenic primers (lowers mutation efficiency), and strand displacement activity (lowers mutation efficiency), all of which increase with increasing temperature.

For the standard QuikChange method, between 12 (point mutations) and 18 (insertions and deletions) cycles produce optimal mutation frequencies and number of colonies. In contrast, both mutation frequency and colony number increase with increasing cycle number in the QuikChange Multi-Site procedure (FIG. 5). For example, mutation frequency and colony number increased from 33% to 53% (3-site mutation frequency) and from 150 cfus to 1200 cfus, respectively, when the cycle number was increased from 16 to 30 rounds (65° C. extension temperature).

QuikChange Multi-Site reactions were also cycled using extension times of 1 minute or 2 minutes per kb of target. The numbers of colonies produced were drastically lower for reactions cycled for 1 min/kb instead of 2 min/kb (data not shown).

Example 3

Optimization of FEN-1 Reaction Conditions

The extension temperature (68° C.) employed in the standard QuikChange kit is designed to maximize polymerization while minimizing displacement of mutagenic primers by PfuTurbo DNA polymerase. Above 68° C., PfuTurbo exhibits significant strand displacement activity, and after extending ligation of the newly synthesized mutant plasmid DNA. If the 5' end of the mutant primer is not fully annealed, either due to melting at elevated temperatures (e.g. A/T base pair) or displacement by PfuTurbo ("flap" structure), ligation is expected to be inefficient. If displacement or melting of mutagenic primers at the 5' end is occurring and limiting ligation efficiency, we predicted that FEN-1 should enhance the performance of the QuikChange Multi-Site kit.

Effect of FEN-1

Figure 6:
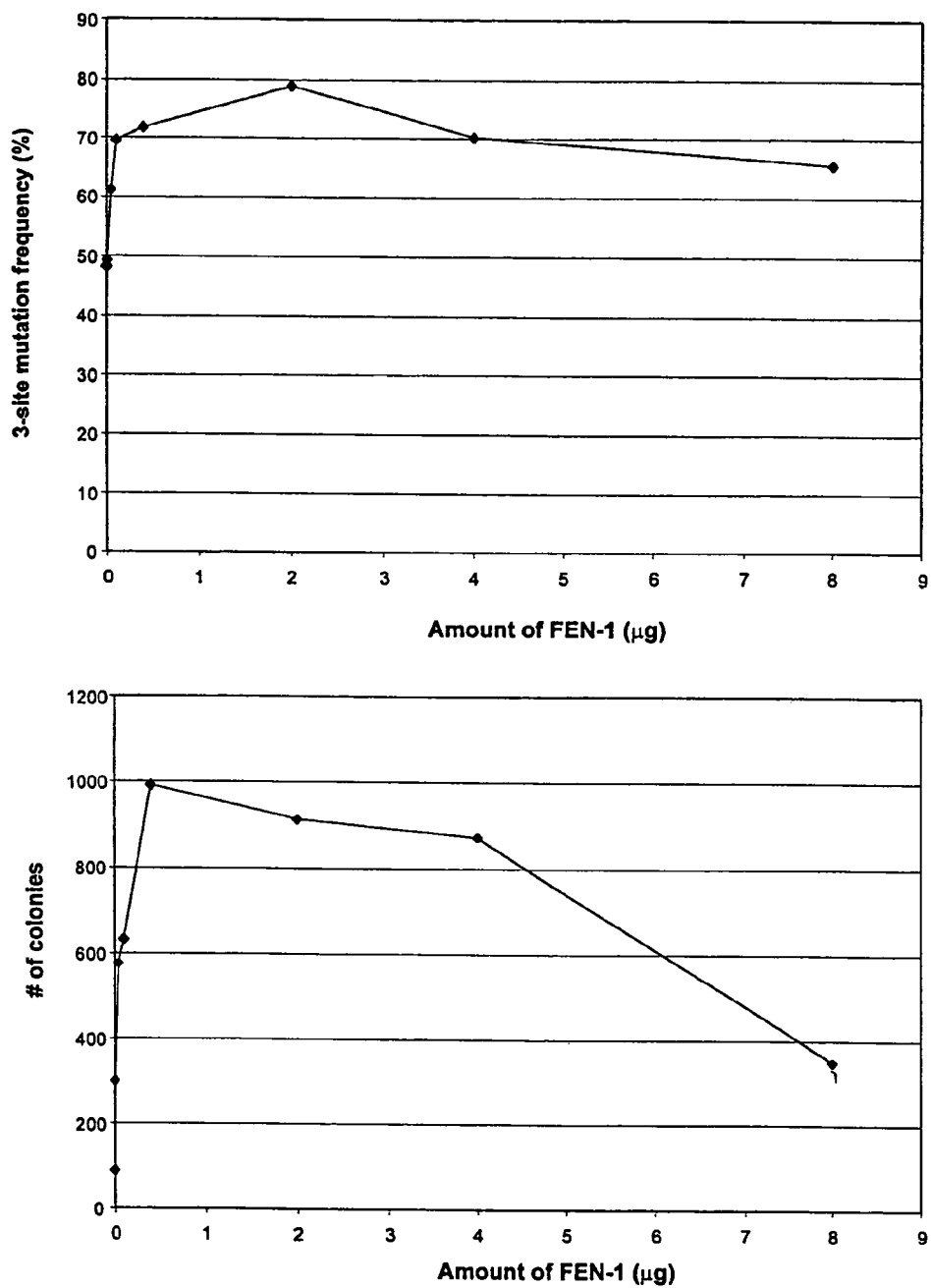
FIG. 6. FEN-1 improves mutation efficiencies and number of transformants. Mutagenesis reactions were carried out with pWS721 and primers QC1, H2, and K2 in the presence of FEN-1. Mutagenesis was performed as described in Methods. Incorporation of all three primers was monitored by blue/white screening. FEN-1 was diluted in FEN-1 final dialysis buffer and 1 ul aliquots were added to each 25 ul reaction.

FIG. 6 shows the effect of adding recombinant P. furiosus FEN-1 to the QuikChange Multi-Site reaction. The 3-site mutation frequency increased from 49% in the absence of FEN-1 to 72-79% in the presence of 400 ng to 4 µg of FEN-1. Even more dramatic improvements were observed in colony number. The number of transformants increased from ~100 cfus to 850-1000 cfus when mutagenesis reactions were performed in the presence of 400 ng to 4 µg of FEN-1.

Example 4

Optimizing Final Reaction Buffer

Figure 7:
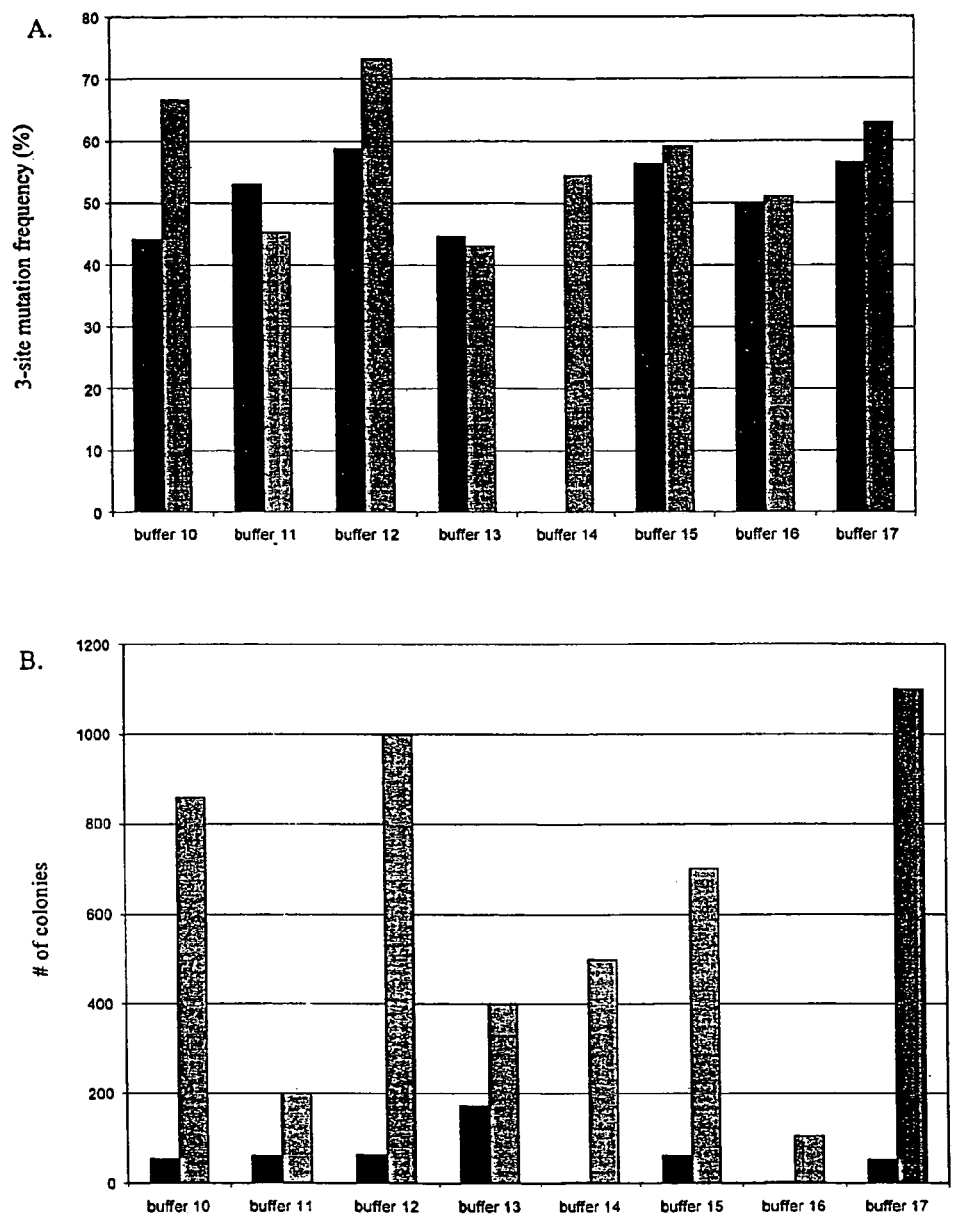
FIG. 7. Final buffer optimization for the QuikChange Multi-Site Kit. Mutagenesis reactions were carried out with pWS721 and primers QC1, H2, and K2 in the absence (black bars) or presence (grey bars) of FEN-1. Mutagenesis was performed as described in Methods. Incorporation of all three primers was monitored by blue/white screening (Panel A). The addition of FEN-1 increased the total number of colonies obtained (Panel B), irrespective of the buffer employed. The "no FEN-1" values are the average of 2 separate experiments.

Additional buffer optimization experiments were performed to identify the best reaction buffer to employ with PfuTurbo DNA polymerase, Tth DNA ligase, and Pfu FEN-1 (400 ng). A series of buffers (#10-17), related to buffers #1 and 2, were prepared and used to determine the optimal KCl and (NH$_4$)$_2$SO$_4$ concentrations and the best Mg$^{2+}$ salt (MgSO$_4$ or MgCl$_2$) to employ (Table 4). Buffer comparisons were carried out in the absence and presence of FEN-1 (FIG. 7). The addition of FEN-1 increased the total number of colonies obtained, irrespective of the buffer employed. The highest mutation efficiencies and colony numbers were achieved using reaction buffers #10, 12, 15, and 17, which contain 20 mM KCl or 10 mM each of KCl and (NH$_4$)$_2$SO$_4$. Slightly better results were obtained in buffers containing MgCl$_2$ instead of MgSO$_4$. Buffer #12 was selected for use in the QuikChange Multi-Site kit (72% 3-site mutation frequency and ~1000 cfus in 25% of transformation). Buffer #12 is similar to cloned Pfu PCR buffer, except that it contains NAD and MgCl$_2$ instead of MgSO$_4$.

Example 5

Verifying Choice of DNA Ligase

Figure 4:
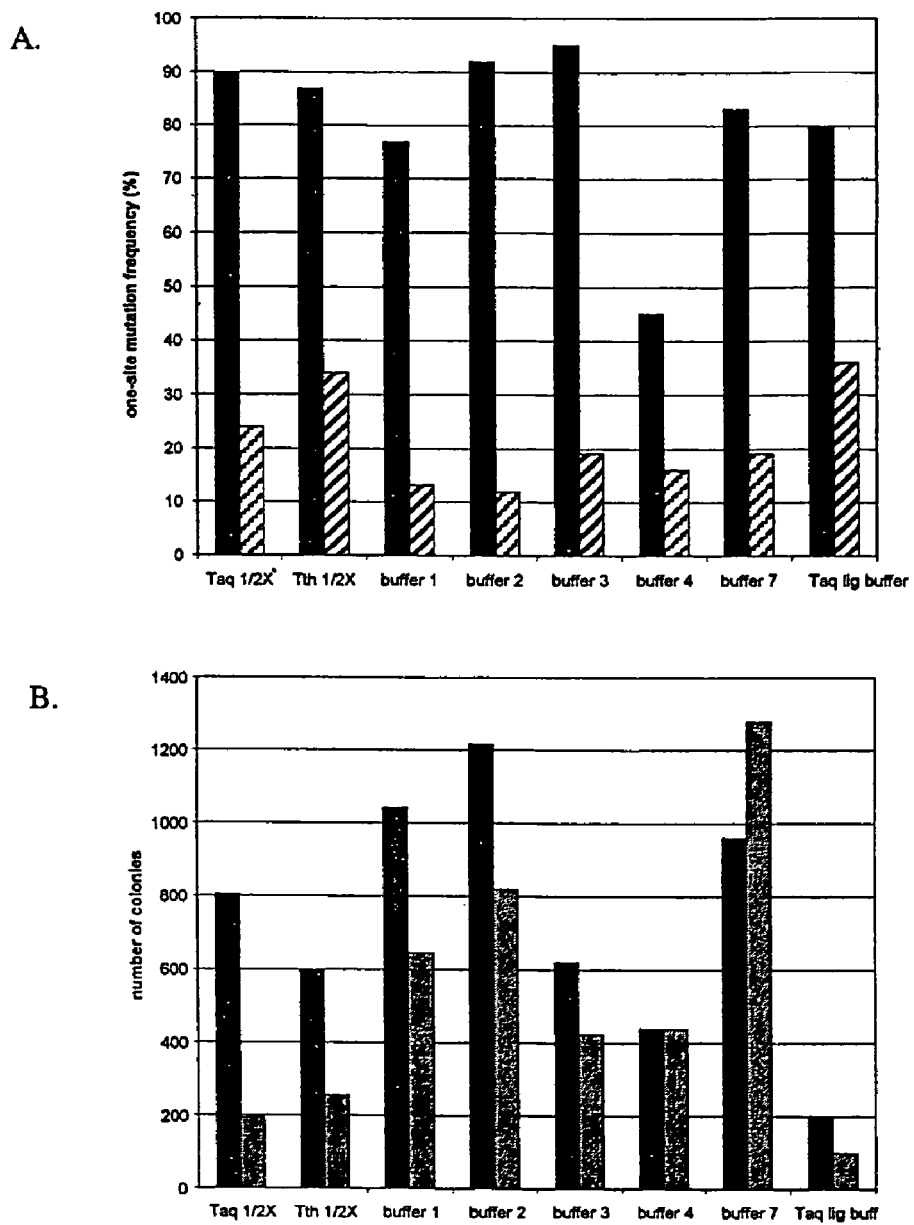
FIG. 4. Preliminary buffer optimization for the QuikChange Multi-Site Kit. Mutagenesis reactions were carried out with pWS and primers QC2 and X3F using the indicated reaction buffers. Mutagenesis was performed as described in Methods except that 2 U Tth DNA ligase, 18 cycles, and no FEN-1 were used. Tth DNA ligase was omitted from reactions shown by the crosshatched bars. Incorporation of the QC2 primer was monitored by blue/white screening, and the total number of colonies (Panel B) and % of clones with a single point mutation (Panel A) were determined. Taq ½× is 0.5× Taq DNA ligase buffer+0.5× cloned Pfu buffer; Tth ½× is 0.5× Tth ligase buffer+0.5× cloned Pfu buffer.
Figure 8:
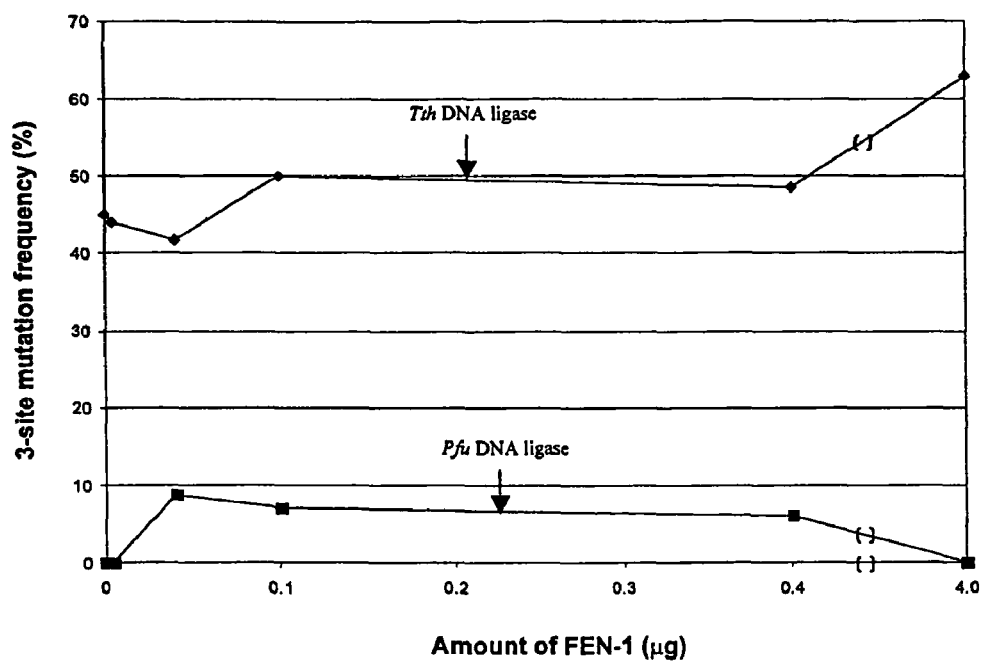
FIG. 8. Activities of thermostable DNA ligases from different sources. Mutagenesis reactions were carried out with pWS721 and primers QC1, H2, and K2 using either Pfu DNA ligase (4 U) or Tth DNA ligase. Mutagenesis was performed as described in Methods, except that buffer #2 containing either 0.1 mM NAD (Tth DNA ligase) or 0.1 mM rATP (Pfu DNA ligase) was used. Incorporation of all three primers was monitored by blue/white screening.
Figure 9:
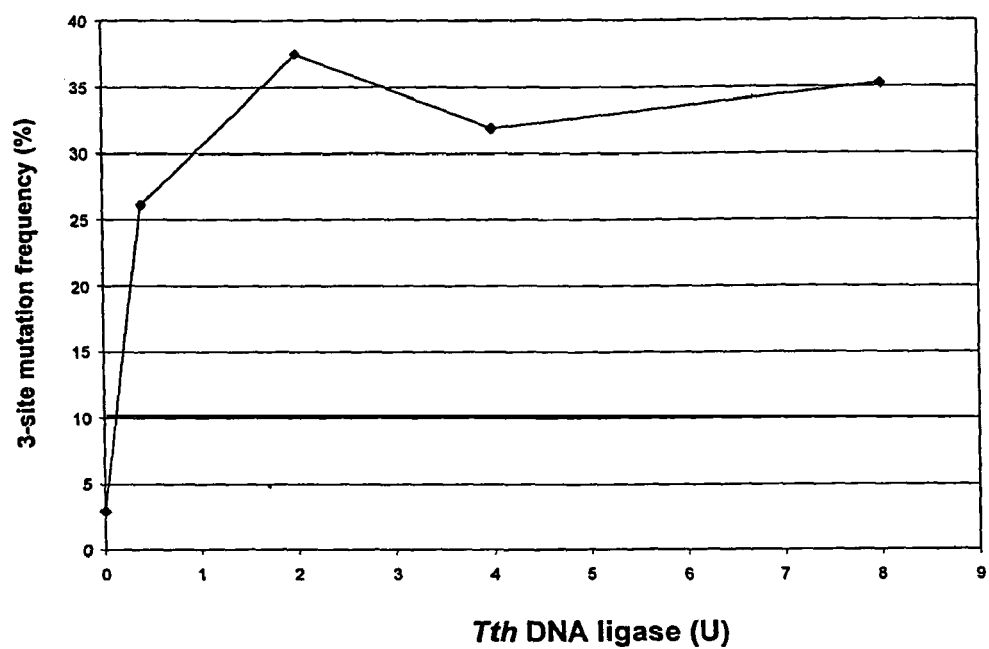
FIG. 9. Optimal Tth DNA ligase concentration for the QuikChange Multi-Site Kit. Mutagenesis reactions were carried out with pWS74 and primers QC1, H2, and K2 using the indicated amount of Tth DNA ligase. Mutagenesis was performed described in Methods, except that reaction buffer #2, 81 cycles, 100 uM each dNTPs, and no FEN-1 were used. Incorporation of all three primers was monitored by blue/white screening.

Previous studies, carried out in the absence of FEN-1, had shown that Tth DNA ligase produced significantly better results than Pfu DNA ligase (Stratagene #600191) (data not shown). These comparisons were repeated in the presence Pfu FEN-1. Since DNA ligase and FEN-1 work together in vivo in lagging strand DNA synthesis, we expected that Pfu DNA ligase would perform better than Tth DNA ligase in reactions employing other Pfu enzymes (DNA polymerase, FEN-1). As shown in FIG. 8, the addition of FEN-I did improve the performance of Pfu DNA ligase in the QuikChange Multi-Site protocol. However, mutation efficiencies (6-9% 3-site mutation frequency) were significantly lower than those achieved using Tth DNA ligase (49-63%).
Tth DNA Ligase Concentration To assess the contribution of DNA ligase to mutation efficiency, mutagenesis reactions were carried out using Pfu-Turbo DNA polymerase, reaction buffer # 2 (0.1 mM NAD), and varying amounts of the Tth DNA ligase preparation. During the development of the QuikChange Multi-Site kit, an old lot of Tth DNA ligase (discontinued Stratagene product; lot #123402A) was employed. As shown in FIG. 9, the highest mutation efficiencies (3-site mutation frequency of 32-38%) were achieved using 2-8 U of Tth DNA ligase (25 µl reaction volume). Consistent with the data shown in FIG. 4A, the addition of DNA ligase is critical to achieving high mutation efficiencies.

Example 6

Final Optimization of the QuikChange Multi-Site Kit

Quik Solution

Figure 10:
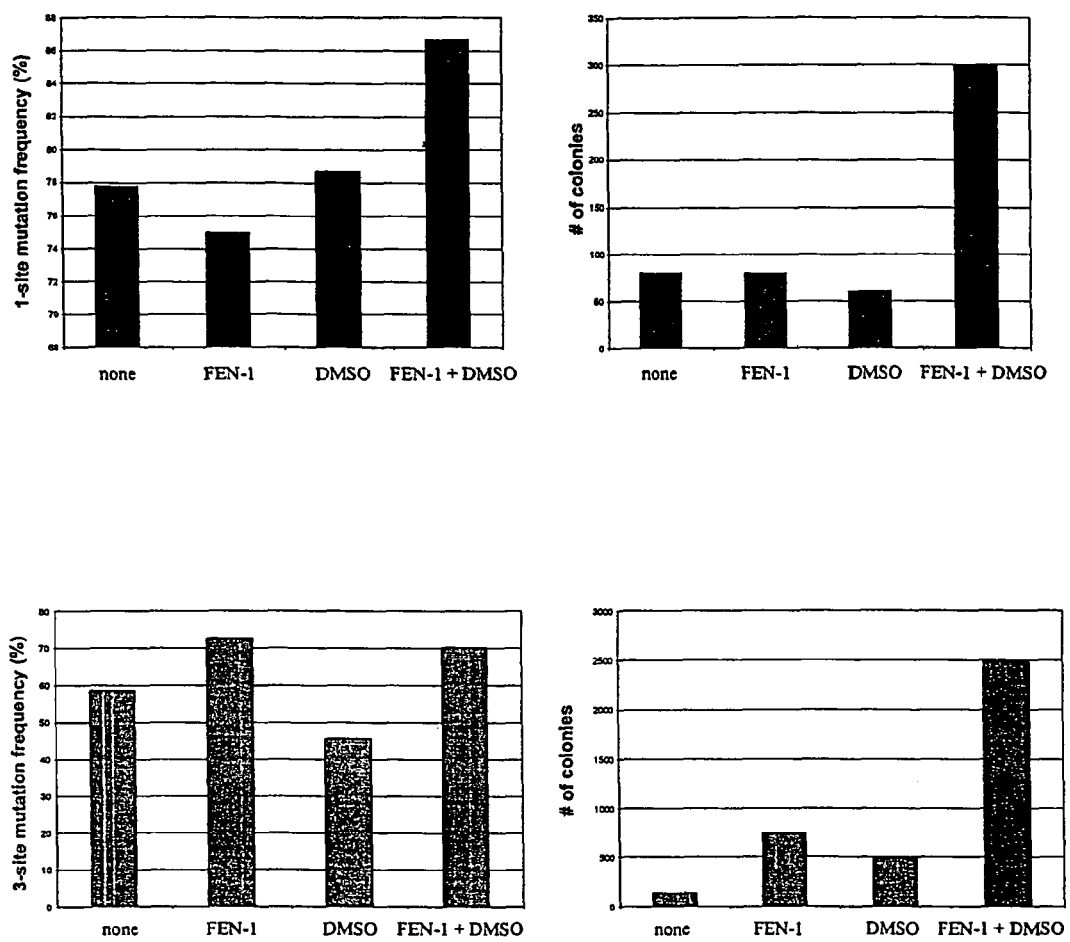
FIG. 10. Effect of DMSO on the QuikChange Multi-Site Kit. Mutagenesis reactions were carried out with pWS and primer QC1 (1-site mutation; black bars) or with pWS721 and primers QC1, H2, and K2 (3-site; grey bars). Mutagenesis was performed as described in Methods, with the following exceptions. FEN-1 was omitted and DMSO was added (3% final concentration) to the indicated reactions. Mutagenesis reactions employing one primer were carried out with 15 ng of pWS, 100 ng of primer QC1, and 1 minute per kb extension times. The values shown for 3-site mutagenesis represent the averages obtained in two independent experiments.
Figure 11:
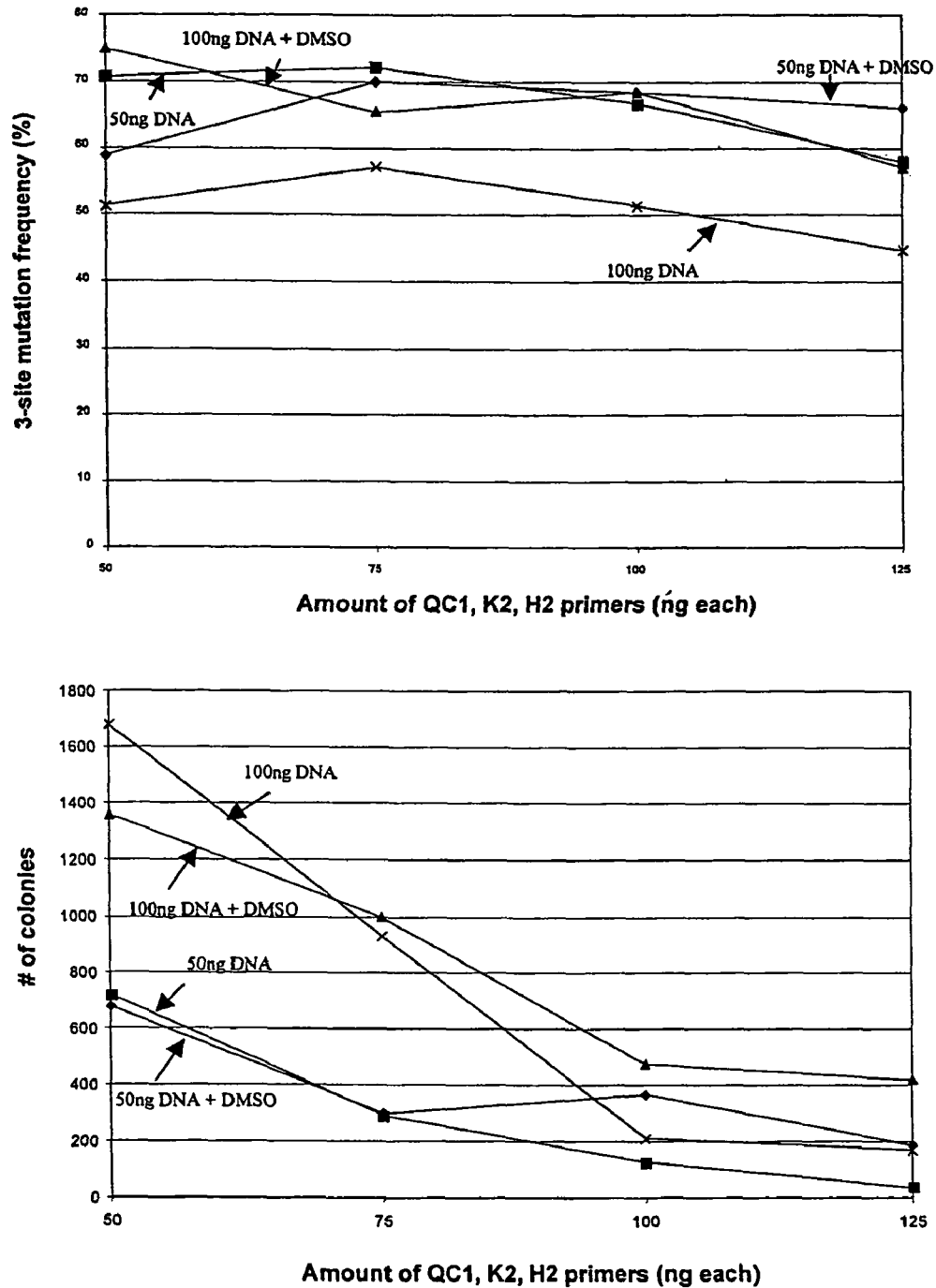
FIG. 11. Optimal concentrations of DNA template and mutagenic primers (QuikChange Multi-Site Kit control). Mutagenesis reactions were carried out as described in Methods using the indicated amounts of each primer (QC1, H2, and K2) and either 50 ng or 10 ng of pWS721 DNA. DMSO was added to a final concentration of 3% to the reactions indicated.

The QuikChange XL kit includes DMSO (Quik Solution) which improves replication of large DNA templates by reducing secondary structures that impede PfuTurbo. DMSO was tested in QuikChange Multi-Site mutagenesis reactions at a final concentration of 3%. In the presence of FEN-1, we found that DMSO increased the number of colonies obtained by 3- to 4-fold, while having little-to-no effect on mutation frequency (FIG. 10). Therefore DMSO (Quik Solution) can be used to facilitate mutagenesis of >4 sites or mutagenesis of long (>5 kb) or difficult plasmid templates.
Optimization of Primer and Template Concentrations We determined the optimal amounts of primers and template to use for the QuikChange Multi-Site kit control. Mutagenesis reactions were carried out, with or without 3% DMSO, using 50 or 100 ng of pWS721 and 50, 75, 100, or 125 ng of each of the three primers (FIG. 11). Using 100 ng of plasmid DNA instead of 50 ng produced more colonies; however, mutation frequencies were significantly lower in reactions employing 100 ng of template (45-57%; 125- to 313-fold molar excess of each primer) compared to 50 ng (58-72%; 250- to 625-fold molar excess of each primer). Curiously, reactions containing DMSO were less sensitive to the amount of plasmid DNA employed, and high mutation frequencies were obtained with both 50 ng (59-66%) and 100 ng (57-75%) of plasmid (FIG. 11). With 50 ng of plasmid DNA, 50-75 ng of each primer produced the highest mutation frequencies (71-72%), and the number of transformants obtained decreased with increasing primer concentration.

Figure 12:
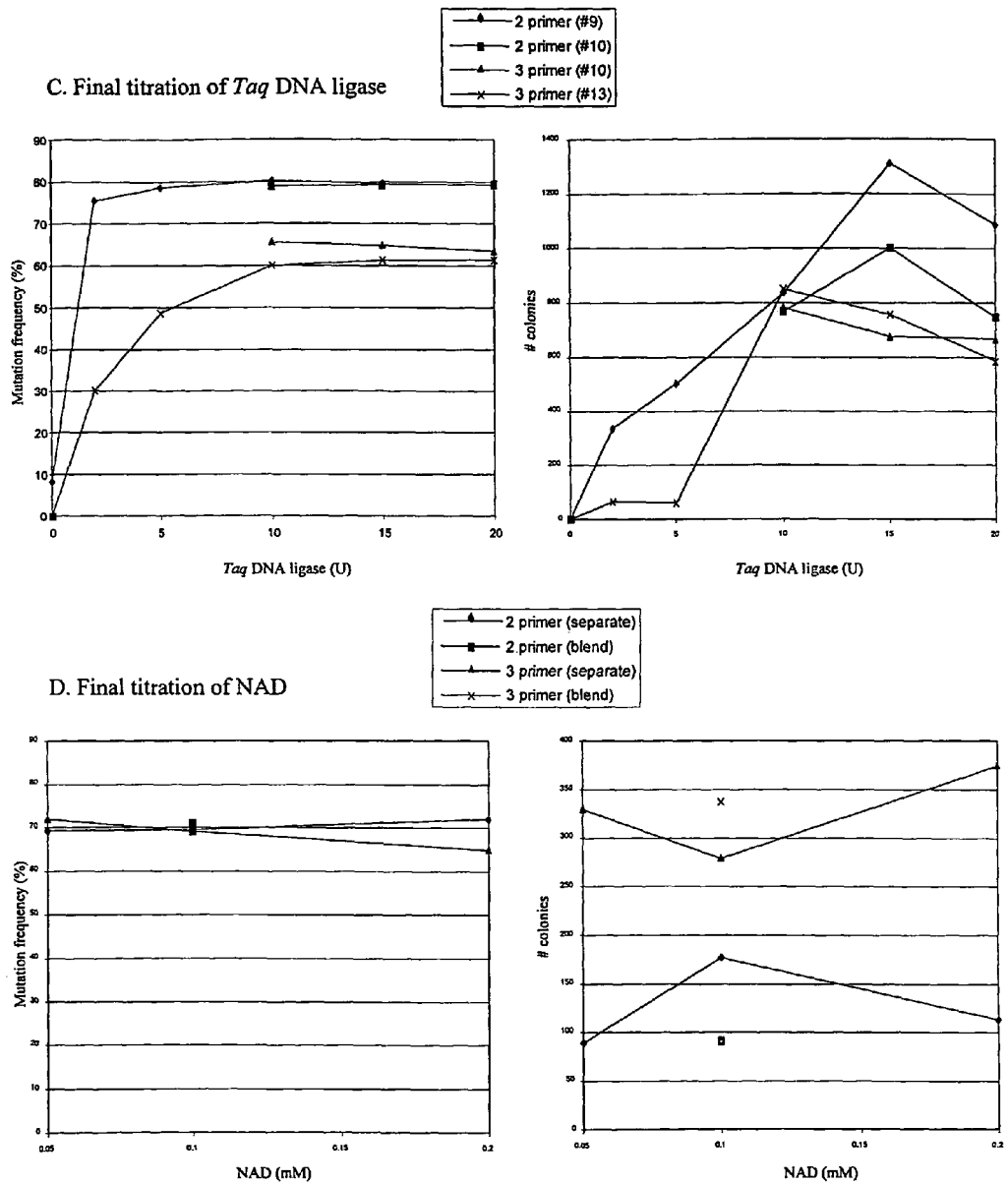
FIG. 12. Final optimization of QuikChange Multi-Site enzyme blend and NAD buffer concentration. Mutagenesis reactions were carried with pWS721 and primers QC1, H2, and K2 (3 primers) or with primers QC1 and K2 (2 primers), as indicated. Reactions employed varying concentrations of: A) PfuTurbo DNA polymerase; B) FEN-1 (lot: SCS #2, SCS #3, or SCS #4); C) Taq DNA ligase; or D) NAD. In these studies, Production-grade lot(s) of buffer #12 and each enzyme were used. Except where varied, each reaction contained 2.5 U PfuTurbo DNA polymerase, 20 U Taq DNA ligase, 400 ng FEN-1 (SCS#3), and 0.1 mM NAD. In panel A, the square shows the performance of a premade blend (1.25 U PfuTurbo, 400 ng FEN-1, 20 U Taq DNA ligase). In panel C, results are shown for 2 independent experiments (#9, 10, or 13), while in panel D, titration results ("separate") are compared with those obtained using a premade buffer ("blend"). All values are the mean of 2 mutagenesis reactions and duplicate platings.

Reduced performance at high primer amounts may be related to general inhibition of PfuTurbo DNA polymerase by excess amounts of DNA (data not shown). Therefore, mutagenesis systems employing more than 3 primers may require the use of lower primer amounts to achieve sufficient colony numbers. To address this possibility, we also carried out mutagenesis with 12.5, 25, 50, 75, 100, or 125 ng of each of 5 different primers (QC1, K2, H2, K2R, K3R). As expected, the number of colonies obtained decreased from 279 cfus (12.5 ng primer) to 3 cfus (125 ng primer; 5% transformed cells), with increasing primer amount. In contrast, mutation frequencies (only QC1, K2, and H2 were monitored) were significantly lower in reactions employing 12.5 ng or 25 ng of each primer instead of 50-125 ng (data not shown). 50 ng (4-5 primers) or 100 ng (1-3 primers) of each primer (~30-34 bases long) with 50 ng (<5 kb) to 100 ng (>5 kb) of plasmid DNA may be used.
Final Optimization of Enzyme Blend and NAD Concentration Finally, we determined the optimal concentrations of Pfu DNA polymerase, Taq DNA ligase, and FEN-1 for use in the QuikChange Multi-Site enzyme blend. These studies employed Production-grade lot(s) of each enzyme, as well as a Production lot of reaction buffer #12. As shown in FIG. 12 panel A, increasing the number of units of PfuTurbo DNA polymerase from 1.25 U to 2.5 U increases both mutation frequency (6-13% increase for 3-site mutation) and number of transformants (3-4-fold). Titration experiments with 2.5 U PfuTurbo DNA polymerase, 20 U Taq DNA ligase, and varying amounts of 3 different R&D/Production lots of *P. furiosus* FEN-1, showed that the highest mutation frequencies (60-68%) and colony numbers (500-650; 5% of transformation) are achieved using 400 ng and 2 µg of FEN-1 per 25 p.1 reaction (FIG. 12, panel B). Moreover, the 3 different Production lots of *P. furiosus* FEN-1 provided comparable results. Titration experiments with 2.5 U PfuTurbo DNA polymerase and 400 ng of FEN-1 (SCS 3), showed that 10-20 U of Taq DNA ligase produces similar mutation frequencies using both a 2-primer and 3-primer mutagenesis system (FIG. 12, panel C). However, colony numbers were somewhat higher in reactions employing 10 U (3 primer system) or 15 U (2 primer system) of Taq DNA ligase. Finally, reactions employing 0.05, 0.1, or 0.2 mM NAD produced equivalent mutation frequencies and colony numbers (FIG. 12, panel D).

Based upon these cumulative data, the composition of the QuikChange Multi-Site enzyme blend will be 2.5 U PfuTurbo DNA polymerase, 400 ng of FEN-1, and 15 U Taq DNA ligase per µl (per reaction).

Example 7

Mutagenesis Results Obtained with the QuikChange Multi-Site Kit

Preliminary Blend (1.25 U PfuTurbo per Reaction)

The QuikChange Multi-Site kit was tested with pWS derivatives (4.0 kb) using 1, 2, 3, 4, or 5 mutagenic primers simultaneously. The primers used were 30-34 nucleotides in length, with $T_m$s ranging between 65° C. and 80° C. (Table 2). Mutagenic primers H, X, QC, K3R, and K2R introduce a single point mutation, while primer K incorporates 2 point mutations. Depending on the primer combinations employed, the mutagenic primers have been designed to anneal immediately adjacent (H,K) or close (31-106 bp gaps created by primers K, H, X, QC, and K2R) to each other, or are located more than 1-kb apart (1.1-2.7 kb gaps produced by primers K3R and K2R).

Table 5 summarizes the results obtained for pWS derivatives using 1.25 U PfuTurbo DNA polymerase, 400 ng FEN-1, 4 U Tth/20 U Taq DNA ligase, 100 ng of each primer (except where noted), and 50 ng of plasmid DNA (except where noted).

TABLE 5

Mutation efficiencies achieved with the QuikChange Multi-Site Directed Mutagenesis Kit (1.25 U PfuTurbo DNA polymerase)

| # of sites | DNA template | primers | Quik Solution | # colonies* (25% of transformed cells) | M.F. (%)* | Mean M.F. per system (%) | Mean M.F. per # of primers (%) |
|---|---|---|---|---|---|---|---|
| | pWS Derivatives (4.0 kb) | | | | | | |
| 1 | pWS | QC1 | no | 80# | 75# | 85.4 | 91.3 |
| | | | yes | 300, 5375 | 86.7#, 94.5 | | |
| | pWS | QC2 | yes | 6750 | 97.1 | 97.1 | |
| 2 | pWS72 | QC1, K.2 | no | 400 | 78.7 | 83.3 | 91.3 |
| | | | yes | 500, 2635, 1995, 2735, 8165, 3645 | 77.6, 84.7, 81.9, 81.9, 88.4, 89.1 | | |
| | pWS72 | QC2, K1 | yes | 4750 | 90.8 | 90.8 | |
| | pWS | QC1, K2R | yes | 5875 | 94.6 | 94.6 | |
| | pWS | QC1, K3R | yes | 6750 | 96.4 | 96.4 | |
| 3 | pWS721 | QC1, K2, H2 | no | 500, 1000, 70, 126, 992 | 72, 73.3, 50, 66.7, 71.8 | 65.5 | 57.8 |
| | | | yes | 200, 210, 365, 100-2000 | 70, 52.4, 68.5, 65.2 | | |
| | pWS721 | QC2, K1, H1 | yes | 50-625 | 12.9, 19.5, 30 | 20.8 | |
| | pWS72 | QC1, K2, K2R | yes | 440 | 78.4 | 78.4 | |
| | pWS72 | QC1, K2, K3R | yes | 660 | 66.3 | 66.3 | |
| 4 | pWS72 | QC1, K2, K3R, K2R | no | 92 | 68.7 | 68.7 | 59.8 |
| | pWS721 | QC1, K2, H2, K3R | no | 123 | 46.8 | 50.9 | |
| | | | yes | 211 | 55 | | |
| 5 | pWS721 | QC1, K2, H2, K3R, K2R | yes | 101, 205, 705⁺ | 28.9, 29.5, 32.4⁺ | 30.3 | 30.3 |
| | non-pWS Derivatives | | | | | | |
| 2 | pGenta (~4.6 kb) | R1outI. R1out3 | no | nd | 83@ | 83 | — |

*M.F., mutation frequency. Results shown in bold type were achieved by carrying out transformations with βME and incubating the cells for 1-hour at 37° C. prior to plating (see Materials and Methods).
15 ng plasmid DNA;
⁺50 ng each primer
@mutagenesis verified by elimination of EcoRI restriction sites As shown in Table 5, approximately 90% of the clones produced from reactions employing one or two primers contained the desired mutations (lacZ⁺), based upon blue/white color screening. Using 3, 4, and 5 primers, incorporation of all mutagenic oligos was achieved with mean frequencies of 57.8% (4 systems), 59.8% (2 systems), and 30.3% (1 system), respectively.

The results in Table 5 indicate that primers located immediately adjacent to each other are incorporated as efficiently as primers that are designed to anneal farther apart. For example, the QC1/K2/H2 (0 and 76 bp gaps), QC1/K2/K2R (72 and 106 bp gaps), and QC1/K2/K3R (106 and 1044 bp gaps) primers are incorporated with mean mutation frequencies of 65.6%, 78.4%, and 66.3%, respectively. Similarly, QC1/K2 (106 bp gap), QC1/K2R (72 bp gap), and QC1/K3R (1044 bp gap) are incorporated with mean mutation frequencies of 83.3%, 94.6%, and 96.4%, respectively.

With one exception, we obtained comparable mutation efficiencies using primer sets that anneal to the sense and the antisense strands. For example, QC1 and QC2 were incorporated with mutation frequencies of 85.4% and 97.1%, respectively, while the QC1/K2 and QC2/K1 primers were incorporated with mean mutation frequencies of 83.3% and 90.8%, respectively. However, with the 3-primer system QC/K/H (H and K primers anneal next to each other), we observed a significant difference between the mutation frequencies obtained using the sense (QC1/K2/H2; 65.6%) and the antisense (QC2/K1/H1; 20.8%) primer sets. Low mutation frequencies were also obtained when a second preparation of primer H1 was used (data not shown). These results indicate that certain DNA sequences may be problematic in the QuikChange Multi-Site method, possibly due to secondary structure (hairpins, etc.) in the primer itself, primer-primer interactions, or secondary structure in one of the denatured template strands. It is not clear how frequently such events may occur, but in the manual, we will recommend that customers having difficulty (<30% mutation frequencies) in obtaining their desired mutations can re-design their primers to anneal to the opposite template strand.

In addition to pWS derivatives, the QuikChange Multi-Site kit (1.25 U PfuTurbo DNA polymerase per reaction) has been used to eliminate two EcoR1 sites from a 4.6 kb pBS plasmid containing the Genta DNA polymerase gene. Loss of both EcoRI restriction sites was observed in 5 of the 6 plasmid DNA clones tested (83% mutation efficiency).

Final Blend (2.5 U PfuTurbo)

Additional mutagenesis was performed using the optimized QuikChange Multi-Site enzyme blend, containing 2.5

U PfuTurbo DNA polymerase, 400 ng FEN-1, and 20 U Taq DNA ligase per μl (per reaction) (Table 6). We also determined the efficiency of mutagenizing larger plasmid templates, using the old pWS 5.7-kb QuikChange kit control, which contains one stop codon at position 792 bp in the lacZ gene. Previous studies with the standard QuikChange kit have shown that the number of transformants obtained decreases as the size of the plasmid DNA template increases. With the standard kit, higher numbers of colonies can be achieved by using DMSO (QuikSolution) and XL10 Gold ultracompetent cells (e.g., QuikChange XL kit improvements) and by employing higher DNA template amounts (>50 ng). Except where noted, mutagenesis studies were carried in the absence of QuikSolution, using 100 ng of each primer and 50 ng of plasmid DNA.

TABLE 6

Mutation efficiencies achieved with the QuikChange Multi-Site Directed Mutagenesis Kit (2.5 U PfuTurbo DNA polymerase)

| # of primers | plasmid size (kb) | sense/ antisense primers | nucleotides changed (bp) | # colonies (25% cells) | M.F. (%) |
|---|---|---|---|---|---|
| 1 | 4.0 | sense | 792 | 10250 | 97.5 |
|   | 4.0 | antisense | 792 | 5150 | 97.2 |
|   | 5.7 | sense | 792 | 1420 | 87.1 |
|   | 5.7 | antisense | 792 | 6305 | 92.4 |
|   | 7.9@ | sense | 1973 | 25*, 65• | 25*, 39• |
| 2 | 4.0 | sense | 656/657, 792 | 2480 | 86.7 |
|   | 4.0 | antisense | 656/657, 792 | 2590 | 86.8 |
|   | 5.7 | sense | 792, 900 | 875# | 15.6# |
|   | 5.7 | sense | 792, 1973 | 725# | 62.9# |
| 3 | 4.0 | sense | 656/657, 792, 900 | 1720 | 65.5 |
|   | 4.0 | sense | 656/657, 792, 1973 | 2150 | 82.2 |
|   | 5.7 | sense | 792, 900, 1973 | 155, 1660* | 15.1, 35.2* |
| 4 | 4.0 | sense | 656/657, 689, 792, 900 | 1445 | 39.0 |
|   | 4.0 | sense | 656/657, 689, 792, 1973 | 1240 | 53.0 |
|   | 4.0 | sense | 656/657, 792, 900, 1973 | 1470$^E$, 940 | 44.1$^E$, 74.0 |
|   | 4.3$ |  |  | 1063 | 10 |

75 ng plasmid DNA;
*100 ng plasmid DNA;
•200 ng plasmid DNA;
$^E$50 ng of each primer
@pCMVLacI plasmid was mutated with primer K3R; mutation frequency was determined by Kpn I restriction digestion
$GFP-containing plasmid (phrGFP-1) was mutated with primers Epro1, Epro2, Epro3, and Epro4, where primer Epro1 introduces 2 point mutations located 5 bases apart (Brenda Rogers); mutation frequency was determined by DNA sequencing.

Using the final optimized QuikChange Multi-Site blend, mutations were incorporated at 2, 3, or 4 sites in the 4.0-kb pWS plasmid with mean mutation frequencies of 86.8%, 73.9%, and 55.3%, respectively. Therefore, at least for moderately-sized plasmids, point mutations can be introduced at up to 4 different sites simultaneously, with minimal downstream sequence analysis required (sequence ~2 clones per mutagenesis reaction). Although we have not determined the maximum number of point mutations that can be incorporated per mutagenic primer, the standard QuikChange method has been used to incorporate up to 4 point mutations (adjacent and separated bases) per primer.

When larger templates (5.7-kb and 7.9-kb) were employed, we observed a significant reduction in both mutation efficiency and numbers of transformants (Table 6). For example, 2 and 3 primers were incorporated into the 5.7-kb pWS plasmid with mutation frequencies of 39.3% (75 ng plasmid; mean for 2 systems) and 27.4% (mean for 25-100 ng plasmid; 1 system), respectively. As expected, higher colony numbers, but not higher mutation efficiencies, were achieved by increasing the amount of the 5.7-kb plasmid in the reaction. For example, reactions employing 25 ng, 50 ng, 75 ng, or 100 ng of pWS 5.7 kb (QC1, K2R, K3R primers) produced the following number of colonies and mutation efficiencies: 55 cfus (37.8%), 155 cfus (15.1%), 375 cfus (21.3%), and 1660 cfus (35.2%), respectively. Additional experiments have shown that DMSO (e.g., 3%) improves the efficiency of multi-site mutagenesis of larger plasmids.

In addition to pWS test systems, the optimized QuikChange multi-site blend was used to make 5 point mutations simultaneously in GFP, using 4 mutagenic primers. Of the 20 clones sequenced, 2 were identified which contained all 5 point mutations (10% mutation efficiency, Table 6; 6 clones incorporated 1 primer and 5 clones each incorporated 2 or 3 primers). Approximately 300 bases of sequence was analyzed per clone. With the exception of intended point mutations, there were no additional mutations identified in any of the 20 GFP clones (data not shown).

As shown in Table 6, we are recovering approximately 90-680,000 cfus from mutagenesis reactions employing one primer and 40-170,000 cfus from reactions employing two primers (4.0-kb to 5.7-kb plasmids, entire reaction transformed and plated). Although researchers generally don't need more than 10 transformants for most applications, high numbers of transformants are required when constructing site-specific random mutant libraries using degenerate primers. The QuikChange Multi-Site kit produces enough colonies to ensure representation of all possible mutants when 3-4 codons are randomly mutagenized and combined (>32 cfus for random mutagenesis of 1 codon (NNX, where N=25% each G, C, A, T and X=50% G and T); ≧1024 cfus for random mutagenesis of 2 codons); ≧32,768 cfu for random mutagenesis of 3 codons.

Example 8

Mutagenesis Using Degenerate Primers

Reactions were carried out as described in example 1 except that different primers and templates were used.

The template used was a DNA encoding exo⁻ JDF-3 DNA polymerase (D141A/E143A) in pBlueScript (5.2 kb).

The primers used were degenerate at the codons corresponding to amino acids 410 (CCT) and 485 (GCC): 410: TTT CGT AGT CTC TAC NNX TCA ATC ATA ATC ACC (SEQ ID NO:14); 485: GAT TAC AGG CAA CGC NNX ATC AAG ATT CTC GCC (SEQ ID NO: 15); where positions denoted with N were synthesized with 25% each G, C, A, and T and those denoted with X were synthesized with 50% each G and T.

Clones were randomly isolated and sequenced to determine the % of clones with mutations. As shown in Table 7, 53-60% of the transformants contained mutations and a variety of amino acid side chain substitutions were produced (Table 8). In experiments where 2 degenerate primers were used, 13% of the clones incorporated mutations at both sites, while additional 37% clones contained one mutation at either amino acid 410 or 485 (Table 8).

TABLE 7

Mutation frequencies generated with degenerate primers with the QuikChange Multi-Site Directed Mutagenesis Kit (2.5 U PfuTurbo DNA polymerase)

| degenerate amino acids | $T_{anneal}$ | number of clones* | M.F. (%) | Type of mutations |
|---|---|---|---|---|
| 410 | 55° C. | 22,000 | 53 | 14/30 clones contained the wild type CCT codon |
|  | 45° C. | 6,000 | 60 | 4/10 clones contained the wild type CCT codon |
| 410/485 | 55° C. | 2,000 | 13 (50% with one mutation) | 2/16 410/485 mutations 1/16 485 mutation only 5/16 410 mutation only 8/16 clones contained the wild type CCT codon |

*6% of reaction transformed

TABLE 8

Amino acid change in JDF-3 Mutants from degenerate 410 library:

| Clone | codon | amino acid |
|---|---|---|
| wt | CCT | P |
| 1 | CCG | P |
| 2, 9 | ATG | M |
| 15, 16, 26 | GGT | G |
| 18 | CTG | L |
| 30 | ATT | I |
| 4, 13 | CAT | H |
| 10, 27 | CAG | Q |
| 19 | TTG | W |
| 20 | TCT | S |
| 22 | ACT | T |
| 23 | CGT | R |

Example 9

Comparison between Sawano Method and QuikChange Multi-Site-Kit

The QuikChange Multi-site kit is compared with the original Sawano method for mutagenesis as described in the above examples. Table 9 summarizes the results.

The use of FEN-1, PEF and optimized reaction buffer combined with optimized cycling conditions results in a significant improvement in both mutation frequency and the numbers of transformants. The high number of transformants produced ensures as many mutants as possible when carrying out DNA shuffling experiments or constructing libraries with 3-4 degenerate codons.

TABLE 9

| Enzyme mixture | Cycling Conditions | Post-Dpn I Cycling | 2 primer mutagenesis | | 3 primer mutagenesis | |
|---|---|---|---|---|---|---|
|  |  |  | % mutants | # colonies* | % mutants | #colonies* |
| Sawano | Sawano | yes | 10.1 | 159 | 39.5 | 544 |
| Sawano | Sawano | no | 27.4 | 124 | 34.1 | 176 |
| Stratagene | Sawano | no | 74.8 | 2618 | 56.2 | 4396 |
| Sawano | Stratagene | no | 45.1 | 82 | 46 | 100 |
| Stratagene | Stratagene | no | 75.8 | 54,980 | 66.2 | 58,980 |

*entire transformation plated

Enzyme Mixtures:

| | Sawano | Stratagene |
|---|---|---|
| Pfu | 2.5 U | 2.5 U |
| Turbo (PEF) | — | 2 U |
| Taq DNA ligase | 20 U | 15 U |
| FEN-1 | — | 400 ng |
| 1× buffer | Pfu:Taq ligase (1:1) | Pfu (except it contains 2 mM $MgCl_2$ instead of $MgSO_4$) |
| dNTPs | 200 μM | 200 μM |
| primers | 100 ng each | 100 ng each |
| plasmid DNA | 50 ng | 50 ng |
| NAD | 1 mM | 0.1 mM |
| reaction volume | 50 μl | 25 μl |

Cycling Conditions:

| | Sawano | Stratagene |
|---|---|---|
| preincubation | 65° C., 5 minutes | |
| initial denaturation | 95° C., 2 minutes | 95° C., 1 minute |
| cycling | 95° C., 30 seconds | 95° C., 1 minute |
| | 55° C., 30 seconds | 55° C., 1 minute |
| | 65° C., 7 minutes | 65° C., 8 minutes |
| # cycles | 18 | 30 |
| final incubation | 65° C., 7 minutes | none |
| post Dpn I cycling | 95° C., 30 seconds, followed by 2 cycles of 95° C., 30 seconds 55° C., 1 minute 70° C., 7 minutes | none |

Example 10

DNA Shuffling Using PfuTurbo and FEN-1

Figure 13:
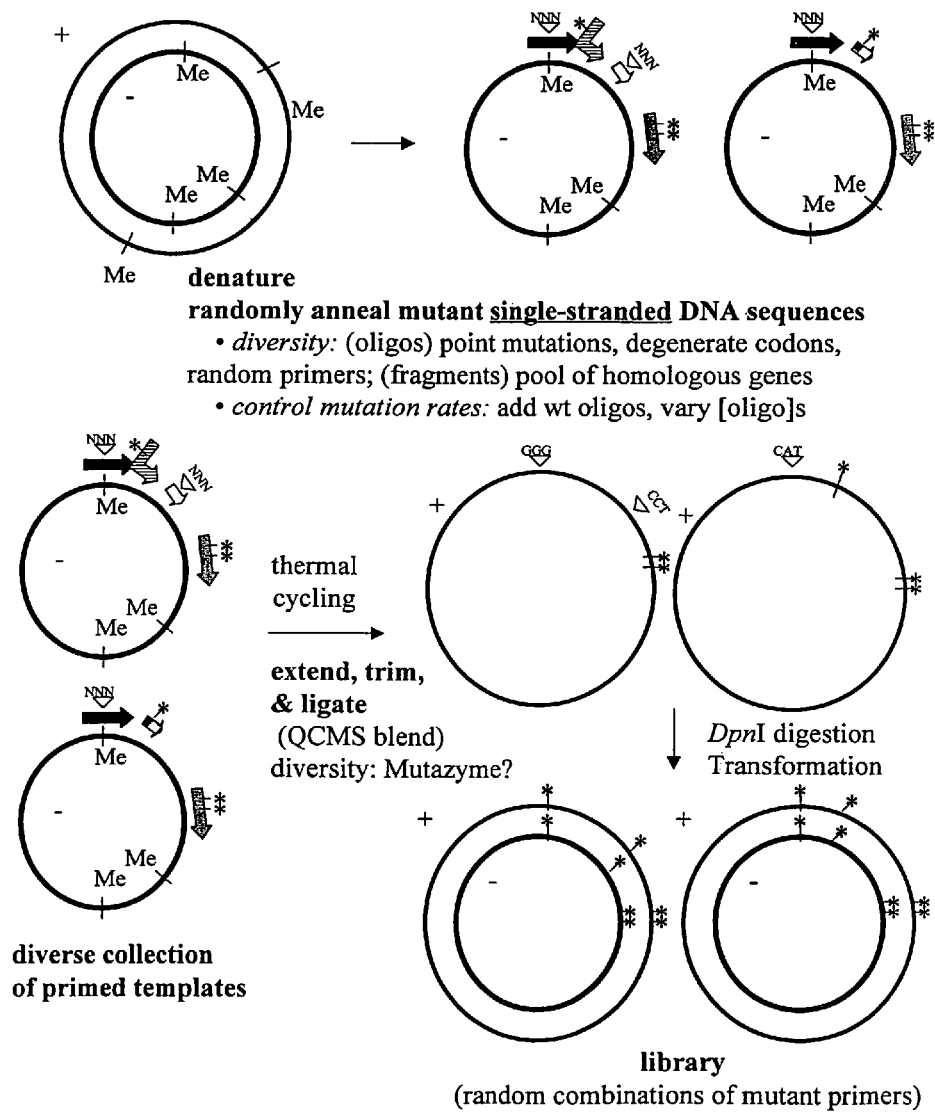
FIG. 13. DNA shuffling with the Quick Change Multi Kit.

The QuikChange Multi-site kit was tested for DNA shuffling (FIG. 13).

GFP-containing plasmid (phrGFP-1) and primers Epro1, Epro2, Epro3, and Epro4 were used to mutagenize GFP. The use of 4 primers can lead to a total of 16 possible outcomes (see FIG. 14).

```
Epro 1 (SEQ ID NO: 16):
CCA GGG CGC CCC Act GCC aTT CGC CTT CG

Epro 2 (SEQ ID NO: 17):
GCA ACT TCC CgA ACG ACG GCC CgG TGA TGA AGA AG

Epro 3 (SEQ ID NO: 18):
CCA GAG CTT CCC gGC CGG CTT CGT G

Epro 4 (SEQ ID NO: 19):
CAT CCT GAG CCC gGC CTT CCA GTA CG
```

Figure 14:
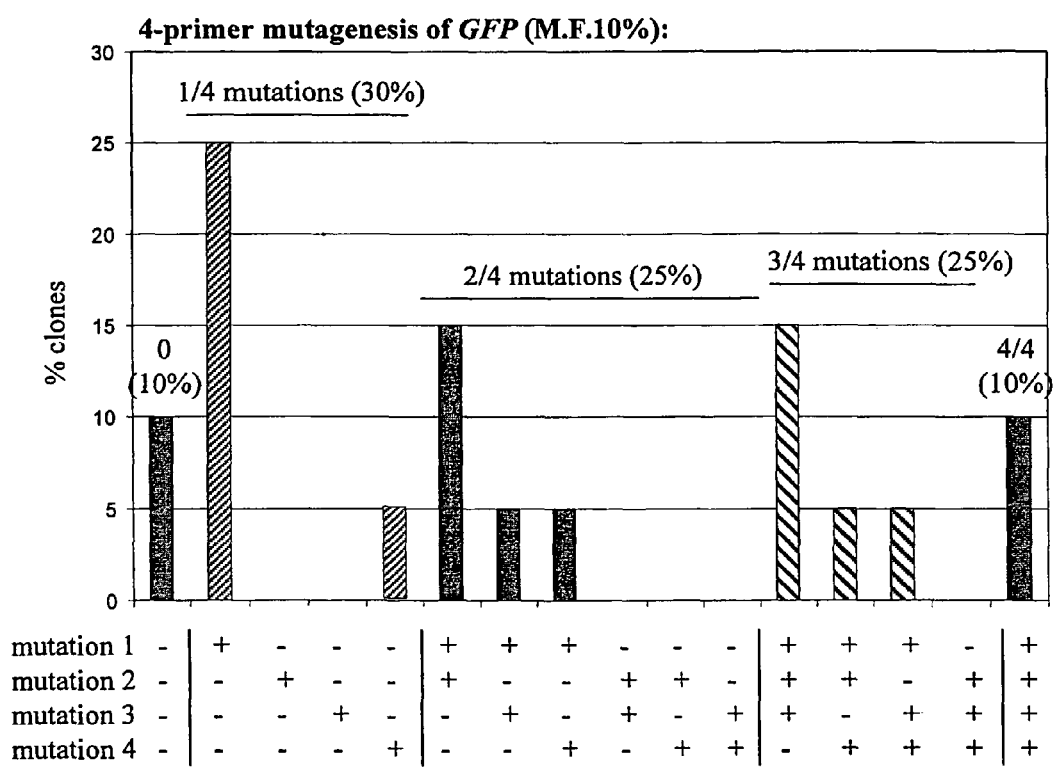
FIG. 14. "Shuffling" of mutagenic primers in Quick-Change Multi Kit. In multiple primer systems, mutagenic primers are randomly combined to produce a diverse collection of mutants. 4-primer mutagenesis of GFP gene can lead to 16 possible outcomes. 9 different single, double, triple, or quadruple mutants were isolated.

As shown in FIG. 14, 9 different single, double, triple, or quadruple mutants were isolated. This result demonstrates that this method can be used to create a collection of random combinations by randomly annealing one, two, three, or four different primers to each template molecule.

Other Embodiments

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

The invention claimed is:

1. An isolated composition comprising a DNA polymerase, a thermostable DNA ligase, a mutagenic primer that is specific for a target polynucleotide, the target polynucleotide, and a flap endonuclease.

2. The isolated composition of claim 1, further comprising a selection enzyme.

3. The isolated composition of claim 2, wherein said selection enzyme is a restriction endonuclease.

4. The isolated composition of claim 3, wherein said restriction endonuclease is methylation-dependent.

5. The isolated composition of claim 4, wherein said methylation-dependent restriction endonuclease is selected from the group consisting of: DpnI, Nan II, NmuD I, and NmuE I.

6. The isolated composition of claim 1, wherein said DNA polymerase is a thermostable DNA polymerase.

7. The isolated composition of claim 6, wherein said thermostable DNA polymerase is selected from the group consisting of: Taq DNA polymerase, Pfu DNA polymerase, Tma DNA polymerase, Tli DNA polymerase, KOD DNA polymerase, JDF-3 DNA polymerase, PGB-D DNA polymerase, Tgo DNA polymerase, and *Pyrolobus furmarius* DNA polymerase.

8. The isolated composition of claim 7, wherein said Pfu-DNA polymerase is Pfu-Turbo DNA polymerase.

9. The isolated composition of claim 1, wherein said thermostable DNA ligase is selected from the group consisting of: Pfu DNA ligase, Tth DNA ligase, Taq DNA ligase, *Thermus*

*filiformis* ligase, *Rhodothermus marinus* DNA ligase, *Thermus scotoductus* DNA ligase, and *Bacillus stearothermophilus* DNA ligase.

10. The isolated composition of claim 1, further comprising nicotinamide adenine dinucleotide.

11. The isolated composition of claim 10, wherein said nicotinamide adenine dinucleotide has a concentration from 0.02 mM to 0.2 mM per reaction.

12. The isolated composition of claim 11, wherein said nicotinamide adenine dinucleotide has a concentration of 0.1 mM per reaction.

13. The isolated composition of claim 1, further comprising ATP.

14. The isolated composition of claim 1, wherein said flap endonuclease is a thermostable flap endonuclease.

15. The isolated composition of claim 14, wherein said thermostable endonuclease is selected from the group consisting of: FEN-1 and Dna2.

16. An isolated composition comprising Pfu DNA polymerase, a thermostable DNA ligase, a target nucleic acid for mutagenesis, and flap endonuclease.

17. The isolated composition of claim 16, wherein said Pfu DNA polymerase has a concentration from 1.25 U to 2.5 U per 25 µl reaction, said DNA ligase has a concentration from 10 U to 20 U per 25 µl reaction, and said flap endonuclease has a concentration from 400 ng to 4 µg per 25 µl reaction.

18. The isolated composition of claim 17, further comprising 0.01 mM to 0.2 mM nicotinamide adenine dinucleotide per the reaction.

19. The isolated composition of claim 18, wherein the DNA ligase is Taq DNA ligase and wherein the concentration of said Pfu DNA polymerase is 2.5 U per 25 µl reaction, the concentration of said Taq DNA ligase is 15 U per 25 µl reaction, the concentration of said flap endonuclease is 400 ng per 25 µl reaction, and the concentration of said nicotinamide adenine dinucleotide is 0.1 mM per 25 µl reaction.

20. The isolated composition of claim 1 or 16, further comprising a polymerase enhancing factor.

21. The isolated composition of claim 1 or 16, further comprising DMSO.

22. The isolated composition of claim 1 or 16, further comprising at least one additional primer.

23. The isolated composition of claim 22, wherein said additional primer is a mutagenic primer.

24. A kit comprising a DNA polymerase, a thermostable DNA ligase, a flap endonuclease, a restriction endonuclease, a mutagenic primer that is specific for a target polynucleotide, a control template nucleic acid, and packaging means therefor.

25. The kit of claim 24, further comprising a selection enzyme.

26. The kit of claim 24, wherein said DNA polymerase is Pfu DNA polymerase.

27. The kit of claim 24, wherein said DNA ligase is a Taq DNA ligase.

28. The kit of claim 24, further comprising nicotinamide adenine dinucleotide at a concentration from 0.01 to 0.2 mM per reaction.

29. The kit of claim 24, wherein said flap endonuclease is FEN-1.

30. A kit comprising Pfu DNA polymerase, Taq DNA ligase, a mutagenic primer that is specific for a target polynucleotide, a control template nucleic acid, and FEN-1.

31. The isolated composition of claim 30, wherein said Pfu DNA polymerase has a concentration from 1.25 U to 2.5 U per 25 µl reaction, said DNA ligase has a concentration from 10 U to 20 U per 25 µl reaction, and said flap endonuclease has a concentration from 400 ng to 4 µg per 25 µl reaction.

32. The kit of claim 31, further comprising 0.01 to 0.2 mM nicotinamide adenine dinucleotide per the reaction.

33. A kit comprising 2.5 U Pfu DNA polymerase, 15 U Taq DNA ligase, 400 ng flap endonuclease, and 0.1 mM nicotinamide adenine dinucleotide per 25 µl reaction.

34. The kit of claim 33, further comprising a selection enzyme, which is a restriction endonuclease.

35. The kit of claim 34, wherein said restriction endonuclease is selected from the group consisting of: DpnI, Nan II, NmuD I, and NmuE I.

36. The kit of claim 33, further comprising at least one mutagenic primer.

37. An isolated composition comprising a DNA polymerase, a thermostable DNA ligase, a restriction endonuclease, a target nucleic acid for mutagenesis, and a flap endonuclease.

38. The isolated composition of claim 37, wherein said restriction endonuclease is methylation-dependent.

39. The isolated composition of claim 38, wherein said methylation-dependent restriction endonuclease is selected from the group consisting of: DpnI, Nan II, NmuD I, and NmuE I.

40. The isolated composition of claim 37, further comprising at least one primer.

41. The isolated composition of claim 40, wherein said primer is a mutagenic primer.

42. The isolated composition of claim 41, wherein said mutagenic primer is a degenerate primer.

43. An isolated composition comprising a DNA polymerase, a thermostable DNA ligase, a selection enzyme, a parental target DNA, and a flap endonuclease, wherein said selection enzyme selectively digests the parental target DNA.

44. The isolated composition of claim 43, wherein said DNA polymerase is a thermostable DNA polymerase.

45. The isolated composition of claim 44, wherein said thermostable DNA polymerase is selected from the group consisting of: Taq DNA polymerase, Pfu DNA polymerase, Tma DNA polymerase, Tli DNA polymerase, KOD DNA polymerase, JDF-3 DNA polymerase, PGB-D DNA polymerase, Tgo DNA polymerase, and Pyrolobus funnarius DNA polymerase.

46. The isolated composition of claim 43, wherein said thermostable DNA ligase is selected from the group consisting of: Pfu DNA ligase, Tth DNA ligase, Taq DNA ligase, *Thermus filiformis* ligase, *Rhodothermus marinus* DNA ligase, *Thermus scotoductus* DNA ligase, and *Bacillus stearothermophilus* DNA ligase.

47. The isolated composition of claim 43, further comprising nicotinamide adenine dinucleotide.

48. The isolated composition of claim 43, wherein said flap endonuclease is a thermostable flap endonuclease.

49. The isolated composition of claim 48, wherein said thermostable endonuclease is selected from the group consisting of: FEN-1 and Dna2.

50. The isolated composition of claim 43, wherein said selection enzyme is a restriction endonuclease.

51. The isolated composition of claim 50, wherein said restriction endonuclease is methylation-dependent.

52. The isolated composition of claim 51, wherein said methylation-dependent restriction endonuclease is selected from the group consisting of: DpnI, Nan II, NmuD I, and NmuE I.

53. The isolated composition of claim 43, further comprising at least one primer.

54. The isolated composition of claim 53, wherein said primer is a mutagenic primer.

55. An isolated composition comprising a DNA polymerase, a thermostable DNA ligase, RecJ exonuclease, a target polynucleotide, and a mutagenic primer that is specific for the target polynucleotide.

56. The isolated composition of claim 55, further comprising a selection enzyme.

57. The isolated composition of claim 56, wherein said selection enzyme is a restriction endonuclease.

58. The isolated composition of claim 57, wherein said restriction endonuclease is methylation-dependent.

59. The isolated composition of claim 58, wherein said methylation-dependent restriction endonuclease is selected from the group consisting of: DpnI, Nan II, NmuD I, and NmuE I.

60. The isolated composition of claim 1, 23, or 54, wherein said mutagenic primer is a degenerate primer.

61. The isolated composition of claim 1, 22, 40, or 53, wherein said primer or said additional primer is about 20 to 50 bases in length.

* * * * *

UNITED STATES PATENT AND TRADEMARK OFFICE
CERTIFICATE OF CORRECTION

PATENT NO. : 8,067,556 B2  Page 1 of 1
APPLICATION NO. : 10/198449
DATED : November 29, 2011
INVENTOR(S) : Holly H. Hogrefe et al.

It is certified that error appears in the above-identified patent and that said Letters Patent is hereby corrected as shown below:

On the Title Page, Item (56), under "Other Publications", line 1, delete "Straragene," and insert -- Stratagene, --, therefor.

On the Title Page, Item (56), under "Other Publications", line 3, delete "Betain" and insert -- Betaine --, therefor.

In column 50, line 43, in Claim 45, delete "funnarius" and insert -- furmarius --, therefor.

Signed and Sealed this
Tenth Day of January, 2012

David J. Kappos
*Director of the United States Patent and Trademark Office*

SEQUENCE LISTING

```
<160> NUMBER OF SEQ ID NOS: 20

<210> SEQ ID NO 1
<211> LENGTH: 427
<212> TYPE: DNA
<213> ORGANISM: Artificial Sequence
<220> FEATURE:
<223> OTHER INFORMATION: Synthetic oligonucleotide

<400> SEQUENCE: 1
attaacgctt acaatttcca ttcgccattc aggctgcgca actgttggga agggcgatcg        60
gtgcgggcct cttcgctata cgccagctgg cgaaaggggg atgtgctgca aggcgattaa      120
gttgggtaac gccagggttt tcccagtcac gacgttgtaa aacgacggcc agtgagcgcg      180
cgtaatacga ctcactatag ggcgaattgg gttacgggcc ccccctcgag gtcgacggta      240
tcgattagct tgatatcgaa ttcctgcagc ccgggggatc cactagttct agagcggccg      300
ccaccgcggt ggagctccag cttttgttcc ctttagtgag ggttaattac gcgcttggcg      360
taatcatggt catagctgtt tcctgtgtga aattgttatc cgctcacaat tccacacaac      420
atacgag                                                                427

<210> SEQ ID NO 2
<211> LENGTH: 30
<212> TYPE: DNA
<213> ORGANISM: Artificial
<220> FEATURE:
<223> OTHER INFORMATION: Synthetic oligonucleotide

<400> SEQUENCE: 2
tcgatatcaa gcttatcgat accgtcgacc                                         30

<210> SEQ ID NO 3
<211> LENGTH: 30
<212> TYPE: DNA
<213> ORGANISM: Artificial
<220> FEATURE:
<223> OTHER INFORMATION: Synthetic oligonucleotide

<400> SEQUENCE: 3
ggtcgacggt atcgattagc ttgatatcga                                         30

<210> SEQ ID NO 4
<211> LENGTH: 33
<212> TYPE: DNA
<213> ORGANISM: Artificial
<220> FEATURE:
<223> OTHER INFORMATION: Synthetic oligonucleotide

<400> SEQUENCE: 4
atagggcgaa ttgggtaccg ggccccccct cga                                     33

<210> SEQ ID NO 5
```

```
<211> LENGTH: 33
<212> TYPE: DNA
<213> ORGANISM: Artificial
<220> FEATURE:
<223> OTHER INFORMATION: Synthetic oligonucleotide

<400> SEQUENCE: 5 tcgaggggggg gcccggtacc caattcgccc tat                                    33

<210> SEQ ID NO 6
<211> LENGTH: 33
<212> TYPE: DNA
<213> ORGANISM: Artificial
<220> FEATURE:
<223> OTHER INFORMATION: Synthetic oligonucleotide

<400> SEQUENCE: 6
atagggcgaa ttgggttacg ggccccccct cga                                     33

<210> SEQ ID NO 7
<211> LENGTH: 30
<212> TYPE: DNA
<213> ORGANISM: Artificial
<220> FEATURE:
<223> OTHER INFORMATION: Synthetic oligonucleotide

<400> SEQUENCE: 7
gggatccact agttctagag cggccgccac                                         30

<210> SEQ ID NO 8
<211> LENGTH: 30
<212> TYPE: DNA
<213> ORGANISM: Artificial
<220> FEATURE:
<223> OTHER INFORMATION: Synthetic oligonucleotide

<400> SEQUENCE: 8
gtggcggccg ctctagaact agtggatccc                                         30

<210> SEQ ID NO 9
<211> LENGTH: 30
<212> TYPE: DNA
<213> ORGANISM: Artificial
<220> FEATURE:
<223> OTHER INFORMATION: Synthetic oligonucleotide

<400> SEQUENCE: 9
gggatccact agttatagag cggccgccac                                         30

<210> SEQ ID NO 10
<211> LENGTH: 34
<212> TYPE: DNA
<213> ORGANISM: Artificial
<220> FEATURE:
<223> OTHER INFORMATION: Synthetic oligonucleotide

<400> SEQUENCE: 10
ccatgattac gccaagcgcg caattaaccc tcac                                    34

<210> SEQ ID NO 11
<211> LENGTH: 34
<212> TYPE: DNA
<213> ORGANISM: Artificial
<220> FEATURE:
<223> OTHER INFORMATION: Synthetic oligonucleotide

<400> SEQUENCE: 11
```

```
gtgagggtta attgcgcgct tggcgtaatc atgg                              34
```

<210> SEQ ID NO 12
<211> LENGTH: 30
<212> TYPE: DNA
<213> ORGANISM: Artificial
<220> FEATURE:
<223> OTHER INFORMATION: Synthetic oligonucleotide

<400> SEQUENCE: 12

```
gctcactcat taggtacccc aggctttaca                                   30
```

<210> SEQ ID NO 13
<211> LENGTH: 31
<212> TYPE: DNA
<213> ORGANISM: Artificial
<220> FEATURE:
<223> OTHER INFORMATION: Synthetic oligonucleotide

<400> SEQUENCE: 13

```
ctgattaagc attggtacct gtcagaccaa g                                 31
```

<210> SEQ ID NO 14
<211> LENGTH: 33
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (16)..(17)
<223> OTHER INFORMATION: N = A, C, G, or T
<220> FEATURE:
<221> NAME/KEY: misc_feature
<222> LOCATION: (18)..(18)
<223> OTHER INFORMATION: N = G or T

<400> SEQUENCE: 14

```
tttcgtagtc tctacnnntc aatcataatc acc                               33
```

<210> SEQ ID NO 15
<211> LENGTH: 33
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (16)..(17)
<223> OTHER INFORMATION: N = A, C, G, or T
<220> FEATURE:
<221> NAME/KEY: misc_feature
<222> LOCATION: (18)..(18)
<223> OTHER INFORMATION: N = G or T

<400> SEQUENCE: 15

```
gattacaggc aacgcnnnat caagattctc gcc                               33
```

<210> SEQ ID NO 16
<211> LENGTH: 29
<212> TYPE: DNA
<213> ORGANISM: Artificial
<220> FEATURE:
<223> OTHER INFORMATION: Synthetic oligonucleotide

<400> SEQUENCE: 16

```
ccagggcgcc ccactgccat tcgccttcg                                    29
```

<210> SEQ ID NO 17

```
<211> LENGTH: 35
<212> TYPE: DNA
<213> ORGANISM: Artificial
<220> FEATURE:
<223> OTHER INFORMATION: Synthetic oligonucleotide

<400> SEQUENCE: 17
gcaacttccc gaacgacggc ccggtgatga agaag                                35

<210> SEQ ID NO 18
<211> LENGTH: 25
<212> TYPE: DNA
<213> ORGANISM: Artificial
<220> FEATURE:
<223> OTHER INFORMATION: Synthetic oligonucleotide

<400> SEQUENCE: 18
ccagagcttc ccggccggct tcgtg                                           25

<210> SEQ ID NO 19
<211> LENGTH: 26
<212> TYPE: DNA
<213> ORGANISM: Artificial
<220> FEATURE:
<223> OTHER INFORMATION: Synthetic oligonucleotide

<400> SEQUENCE: 19
catcctgagc ccggccttcc agtacg                                          26

<210> SEQ ID NO 20
<211> LENGTH: 427
<212> TYPE: DNA
<213> ORGANISM: Artificial
<220> FEATURE:
<223> OTHER INFORMATION: Synthetic Construct

<400> SEQUENCE: 20
attaacgctt acaatttcca ttcgccattc aggctgcgca actgttggga agggcgatcg    60
gtgcgggcct cttcgctata cgccagctgg cgaaaggggg atgtgctgca aggcgattaa    120
gttgggtaac gccagggttt cccagtcac gacgttgtaa aacgacggcc agtgagcgcg     180
cgtaatacga ctcactatag ggcgaattgg gttacgggcc cccctcgag gtcgacggta    240 tcgattagct tgatatcgaa ttcctgcagc ccggggatc cactagttct agagcggccg    300
ccaccgcggt ggagctccag cttttgttcc ctttagtgag ggttaattac gcgcttggcg    360
taatcatggt catagctgtt tcctgtgtga aattgttatc cgctcacaat tccacacaac    420
atacgag                                                              427
```